United States Patent [19]

Takeda et al.

[11] Patent Number: 4,590,188

[45] Date of Patent: May 20, 1986

[54] 1,5-BENZOTHIAZEPINE DERIVATIVES AND THEIR PHARMACEUTICAL USE

[75] Inventors: Mikio Takeda, Urawa; Tokuro Oh-ishi, Tokyo; Hiromichi Nakajima, Urawa; Taku Nagao, Tokyo, all of Japan

[73] Assignee: Tanabe Seiyaku Co., Ltd., Japan

[21] Appl. No.: 698,125

[22] Filed: Feb. 4, 1985

[30] Foreign Application Priority Data

Feb. 18, 1984 [GB] United Kingdom ............... 8404324
Feb. 18, 1984 [GB] United Kingdom ............... 8404325
Mar. 10, 1984 [GB] United Kingdom ............... 8406318

[51] Int. Cl.$^4$ ................... A61K 31/55; C07D 281/10
[52] U.S. Cl. ............................. 514/211; 260/239.3 B
[58] Field of Search .................. 260/239.3 B; 514/211

[56] References Cited

U.S. PATENT DOCUMENTS

| | | | |
|---|---|---|---|
| 3,075,967 | 1/1963 | Krapcho | 260/239.3 B |
| 3,309,361 | 3/1967 | Krapcho et al. | 260/239.3 B |
| 3,341,516 | 9/1967 | Krapcho | 260/239.3 B |
| 3,562,257 | 2/1971 | Kugita et al. | 260/239.3 B |

Primary Examiner—Robert T. Bond
Attorney, Agent, or Firm—Scully, Scott, Murphy & Presser

[57] ABSTRACT

Novel 1,5-benzothiazepine derivatives of the formula:

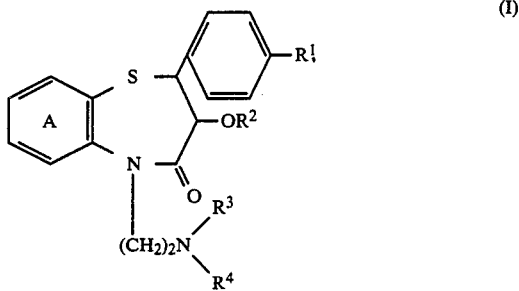

(I)

wherein $R^1$ is lower alkyl or lower alkoxy, $R^2$ is hydrogen atom or lower alkanoyl, each one of $R^3$ and $R^4$ is lower alkyl, Ring A is a substituted benzene ring of the formula:

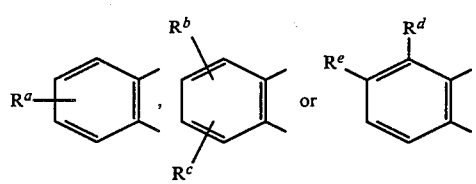

$R^a$ is lower alkyl, lower alkoxy, lower alkylthio or benzyloxy, each one of $R^b$ and $R^c$ is lower alkyl, lower alkoxy or halogen atom, and either one of $R^d$ and $R^e$ is fluorine atom and the other one is hydrogen atom, or a pharmaceutically acceptable acid addition salt thereof are disclosed. Said derivative (I) and its salt are useful as a hypotensive agent and/or a cerebral or coronary vasodilator.

15 Claims, No Drawings

1,5-BENZOTHIAZEPINE DERIVATIVES AND THEIR PHARMACEUTICAL USE

This invention relates to novel 1,5-benzothiazepine derivatives and processes for preparing the same. More particularly, it relates to a compound of the formula:

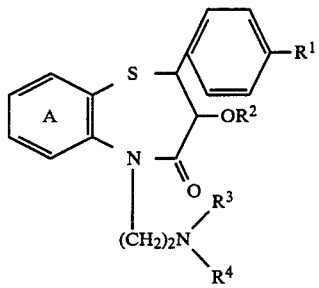

wherein $R^1$ is lower alkyl or lower alkoxy, $R^2$ is hydrogen atom or lower alkanoyl, each one of $R^3$ and $R^4$ is lower alkyl, Ring A is a substituted benzene ring of the formula:

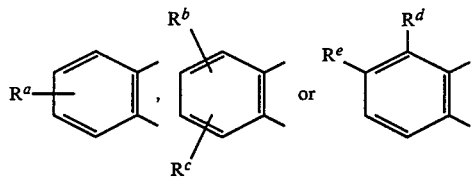

$R^a$ is lower alkyl, lower alkoxy, lower alkylthio or benzyloxy, each one of $R^b$ and $R^c$ is lower alkyl, lower alkoxy or halogen atom, and either one of $R^d$ and $R^e$ is fluorine atom and the other one is hydrogen atom, or a pharmaceutically accetable acid addition salt thereof.

U.S. Pat. No. 3,562,257 discloses various benzothiazepine derivatives such as 2-(4-methoxyphenyl)-3-hydroxy(or acetoxy)-5-[2-(dimethylamino)ethyl]-7-chloro-2,3-dihydro-1,5-benzothiazepin-4(5H)-one. Said U.S. patent also discloses that these benzothiazepine derivatives show an antidepressive activity, tranquilizer activity and/or coronary vasodilating activity.

As a result of various investigations, we have now found that the compound (I) of the present invention or a pharmaceutically acceptable acid addition salt thereof has a potent hypotensive activity and a potent cerebral or coronary vasodilating activity. The compound (I) of the present invention is especially characteristic in that it shows a long-lasting therapeutic effects (e.g., long-lasting hypotensive activity, for example showing activity even 4 hours after administration). For example, when administered orally to spontaneously hypertensive rats (SHR), (±)-cis-2-(4-methoxyphenyl)-3-acetoxy-5-[2-(dimethylamino)ethyl]-8-methoxy-2,3-dihydro-1,5-benzothiazepin-4(5H)-one (hydrochloride) at a dose of 30 mg/kg showed a decrease of about 114 mm Hg and 94 mm Hg in blood pressure of said SHR one hour and 4 hours after administration of the test compound, respectively.

In addition, the compound (I) of the invention shows a potent platelet aggregation-inhibiting activity and is low in toxicity.

Representative examples of the compound of the present invention include those of the formula (I) in which $R^1$ is lower alkyl of one to 4 carbon atoms such as methyl, ethyl, propyl or butyl, or lower alkoxy of one to 4 carbon atoms such as methoxy, ethoxy, propoxy or butoxy; $R^2$ is hydrogen atom or lower alkanoyl of 2 to 4 carbon atoms such as acetyl, propionyl or butyryl; each one of $R^3$ and $R^4$ is lower alkyl of one to 4 carbon atoms such as methyl, ethyl, propyl or butyl; Ring A is a substituted benzene ring of the formula:

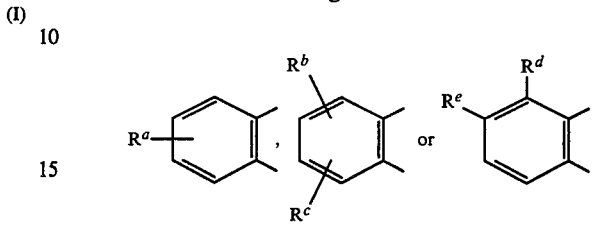

$R^a$ is lower alkyl of one to 4 carbon atoms such as methyl, ethyl, propyl or butyl, lower alkoxy of one to 4 carbon atoms such methoxy, ethoxy, propoxy or butoxy, lower alkylthio of one to 4 carbon atoms such as methylthio, ethylthio, propylthio or butylthio, or benzyloxy; each one of $R^b$ and $R^c$ is lower alkyl of one to 4 carbon atoms such as methyl, ethyl, propyl or butyl, lower alkoxy of one to 4 carbon atoms such as methoxy, ethoxy, propoxy or butoxy, or halogen atom such as chlorine atom, bromine atom or fluorine atom; and either one of $R^d$ and $R^e$ is fluorine atom and the other one is hydrogen atom.

Among them, a preferred subgenus is those of the formula (I) in which $R^1$ is methyl or methoxy. Another preferred subgenus is those of the formula (I) in which $R^1$ is methyl or methoxy, Ring A is a substituted benzene ring of the formula:

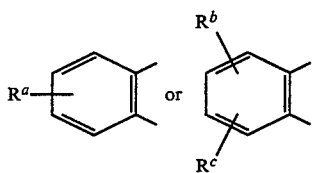

$R^a$ is methyl or methoxy, and $R^b$ and $R^c$ are methyl, methoxy or chlorine atom. Further preferred subgenus is those of the formula (I) in which $R^1$ is methyl or methoxy, $R^2$ is lower alkanoyl, Ring A is a substituted benzene ring of the formula:

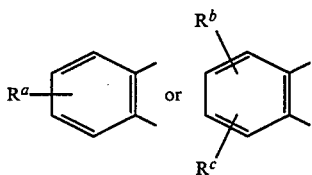

$R^a$ is methyl or methoxy, and $R^b$ and $R^c$ are methyl. Still further preferred subgenus is those of the formula (I) in which $R^1$ is methyl or methoxy, $R^2$ is acetyl, $R^3$ and $R^4$ are methyl, Ring A is a substituted benzene ring of the formula:

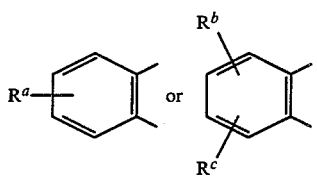

$R^a$ is methyl or methoxy, and $R^b$ and $R^c$ are methyl.

While the compound (I) of the present invention can exist in the form of two stereoisomers (i.e., cis and trans isomers) or four optical isomers (i.e., (+)-cis, (−)-cis, (+)-trans and (−)-trans isomers) due to the two asymmetric carbon atoms involved therein, all of these isomers or a mixture thereof are included within the scope of the invention. Among said isomers, however, the cis isomer, especially the (+)-cis isomer, of the compound (I) is preferred for medicinal use.

According to the present invention, the compound (I) of the present invention can be prepared by the following processes.

PROCESS A

The compound (I) can be prepared by condensing a compound of the formula:

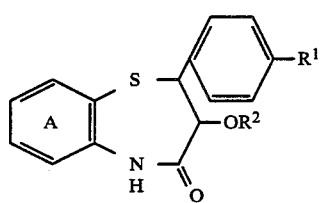

(II)

wherein $R^1$, $R^2$ and Ring A are the same as defined above, or a salt thereof with a compound of the formula:

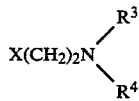

(III)

wherein $R^3$ and $R^4$ are the same as defined above and X is halogen atom, or a salt thereof.

PROCESS B

The compound (I) in which $R^2$ is lower alkanoyl, i.e., a compound of the formula:

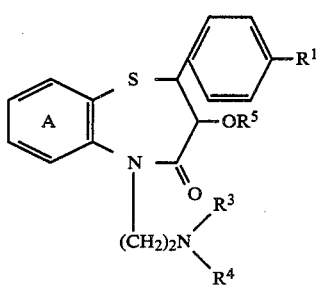

(I-a)

wherein $R^1$, $R^3$, $R^4$ and Ring A are the same as defined above and $R^5$ is lower alkanoyl, can be prepared by condensing a compound of the formula:

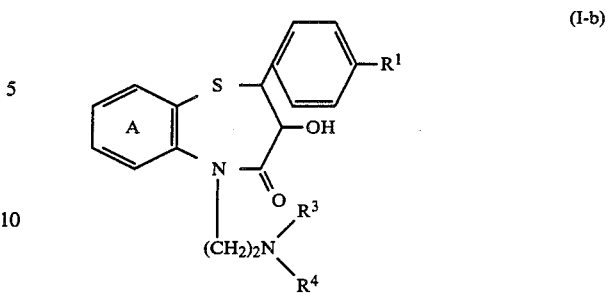

(I-b)

wherein $R^1$, $R^3$, $R^4$ and Ring A are the same as defined above, or a salt thereof with a compound of the formula:

$R^5$—OH (IV)

wherein $R^5$ is the same as defined above, or a reactive derivative thereof.

The condensation of the compound (II) or a salt thereof with the compound (III) or a salt thereof can be carried out in a solvent. Suitable salt of the compound (II) includes, for example, alkali metal salts such as sodium or potassium salts. When the compound (II) is used in a free form, it is preferred to carry out the reaction in the presence of an alkali. The alkali includes, for example, alkali metal hydroxide (e.g., potassium hydroxide, sodium hydroxide), alkali metal carbonate (e.g., potassium carbonate) and alkali metal hydride (e.g., sodium hydride). Examples of the salt of the compound (III) include acid addition salt thereof such as hydrochloride, hydrobromide and so forth. Acetone, ethyl acetate, dimethylsulfoxide, dimethylformamide, acetonitrile, tetrahydrofuran and dioxane are suitable as the solvent. It is preferred to carry out the reaction at a temperature of 0° to 100° C., especially 20° to 70° C.

The condensation of the compound (I-b) or a salt thereof with a reactive derivative of the compound (IV) can be conducted in a solvent in the presence or absence of an acid acceptor. Examples of the salt of the compound (I-b) include acid addition salts thereof such as hydrochloride, hydrobromide and so forth. The reactive derivative of the compound (IV) include, for example, lower alkanoic acid anhydride (e.g., acetic anhydride, propionic anhydride) and lower alkanoyl halide (e.g., acetyl chloride, propionyl chloride, butyryl chloride). The acid acceptor includes, for example, pyridine, triethylamine, N-methylpiperidine, N-methylmorpholine, N-methylpyrrolidine and N-ethyl-N,N-diisopropylamine. Acetic acid, chloroform, dichloromethane, dimethylformamide and tetrahydrofuran are suitable as the solvent. When an excess amount of acetic anhydride is used as the reactive derivative of the compound (IV), it is not always necessary to use the solvent because said acetic anhydride serves as the solvent. It is preferred to carry out the reaction at a temperature of −10° to 140° C., especially at a temperature of 20° to 140° C. if the lower alkanoic acid anhydride is used as the reactive derivative of the compound (IV); or at a temperature of −10° to 100° C. if the lower alkanoyl halide is used as the reactive derivative of the compound (IV).

On the other hand, when the compound (IV) is used in the form of free acid, the condensation thereof with the compound (I-b) or a salt thereof may be carried out in a solvent in the presence of a condensing agent. The condensing agent includes, for example, dicyclohexylcarbodiimide, N,N'-carbonyldiimidazole, 1-methyl-2-halopyridinium iodide (e.g., 1-methyl-2-bromopyridinium iodide), methoxyacetylene and $(C_6H_5)_3P$-$CCl_4$. Methylene chloride, 1,2-dichloroethane, chloroform, benzene, toluene, tetrahydrofuran and dioxane are suitable as the solvent. It is preferred to carry out the reaction at a temperature of 0° to 50° C., especially at 0° to 25° C.

The starting compound (II) or (I-b) of the present invention involves four optical isomers (i.e., (+)-cis, (−)-cis, (+)-trans and (−)-trans isomers) due to the two asymmetric carbon atoms at the 2- and 3-positions of benzothiazepine skeleton. However, since all of the above-mentioned reactions of the invention can be carried out without racemization, the compound (I) of the invention is an optically active form can be readily obtained by the use of the corresponding optically active isomer of the compound (II) or (I-b) as the starting material.

The starting compound (II) of the invention is a novel compound and may be prepared, for example, according to the method shown by the following reaction scheme:

xylene, diphenyl ether, p-cymene) or without solvent. It is preferred to carry it out in an inert gas (e.g., argon). When the compound (II-a) is obtained as a mixture of two stereoisomers (i.e., cis and trans isomers), they may be separated from each other by their difference in solubility in a solvent such as lower alkanol (e.g., ethanol) or by column chromatography.

The reaction of the compound (V) with the compound (VI), i.e., Step (II), can be accomplished by heating a mixture of the compounds (V) and (VI) in a solvent (e.g., toluene, acetonitrile, benzene, dioxane) or without solvent. It is preferred to carry out the reaction at 25° to 110° C. When the trans isomer of the compound (VI) is used as the starting compound, the threo isomer of the compound (VII) is obtained.

The subsequent optional hydrolysis of the compound (VII), i.e., Step (IV), can be conducted by treating it with an alkali metal hydroxide (e.g., potassium hydroxide, sodium hydroxide) or an alkali metal carbonate (e.g., potassium carbonate, sodium carbonate) at 0° to 100° C. in a solvent (e.g., aqueous methanol, aqueous ethanol).

If required, the compound (VIII) thus-obtained may be resolved into each optical isomers by using a resolving agent such as p-hydroxyphenylglycine esters. For example, the optical resolution of (±)-threo-2-hydroxy-3-(2-amino-5-methylphenylthio)-3-(4-methoxyphenyl)-propionic acid or (±)-threo-2-hydroxy-3-(2-amino-4,5-

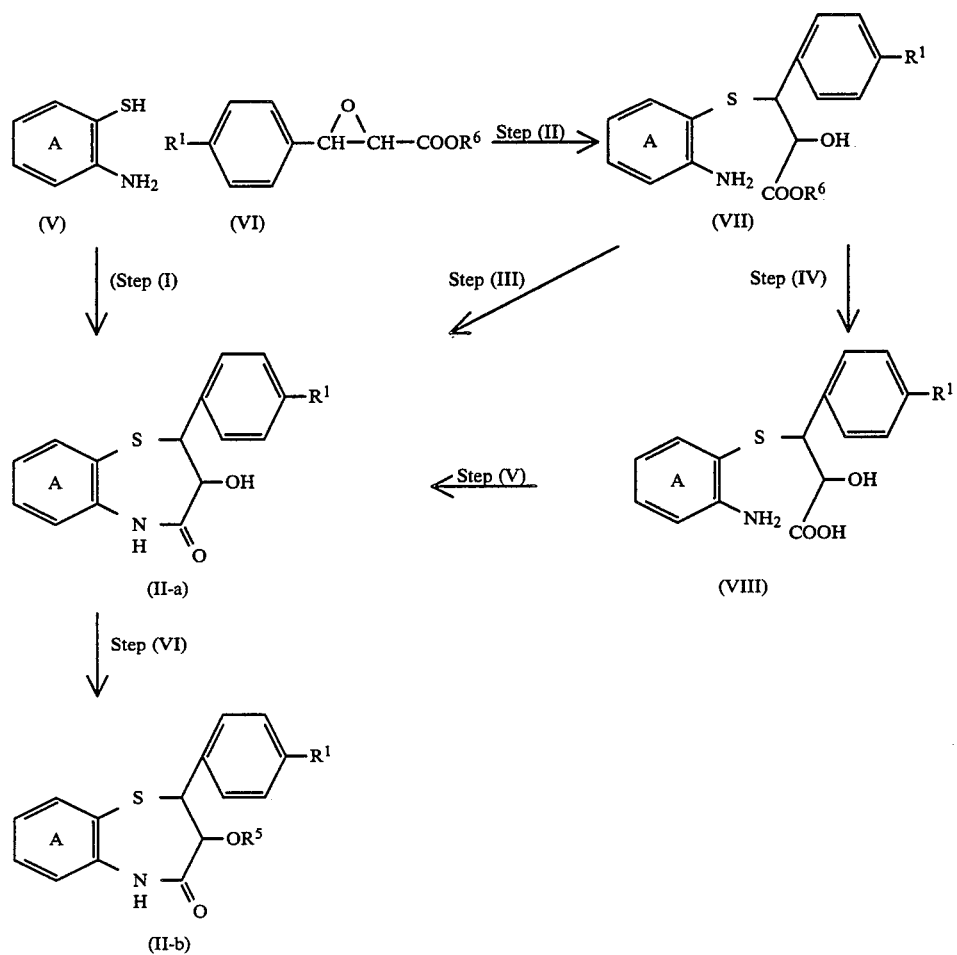

wherein $R^1$, $R^5$ and Ring A are the same as defined above and $R^6$ is lower alkyl.

Step (I) in the above-mentioned reaction scheme can be accomplished by heating a mixture of the compounds (V) and (VI) at 150° to 165° C. either in a solvent (e.g., dimethylphenylthio)-3-(4-methoxyphenyl)propionic acid can be accomplished by the steps of reacting said compound with an optically active p-hydroxyphenylglycine methyl ester to form the diastereoisomeric salts thereof, and separating the diastereoisomeric salts from each other by selective crystallization. Selective crystallization is carried out by recrystallizing the diastereoisomeric salts from a solvent (e.g., methanol, ethanol). After the optical resolution, the optically active compound (VIII) in free form can be recovered by treating the thus-obtained diastereoisomeric salt with an acid (e.g., hydrochloric acid) or an ion-exchange resin.

The intramolecular cyclization of the thus-obtained racemic or optically active compound (VII) or (VIII), i.e., Step (III) or (V), can be carried out by heating at 110° to 160° C. either in a solvent (e.g., xylene) or without solvent. The intramolecular cyclization of the compound (VII) may also be carried out at 0° to 50° C. in the presence of methylsulfinylcarbanion ($CH_3SOCH_2^{\ominus}$) (prepared from dimethylsulfoxide and sodium hydride) in dimethylsulfoxide. Alternatively, the intramolecular cyclization of the compound (VIII) may be carried out at −10° to 70° C. in a solvent (e.g., dimethylformamide, dichloromethane, tetrahydrofuran or a mixture thereof) in the presence of a condensing agent such as dicyclohexylcarbodiimide or a mixture of dicyclohexylcarbodiimide and N-hydroxybenzotriazole.

The subsequent optional acylation of the compound (II-a), i.e., Step (VI), can be accomplished by reacting said compound with a compound of the formula: $R^5$—OH ($R^5$ is the same as defined above) or a reactive derivative thereof in the same manner as described in the acylation of the compound (I-a).

If required, the racemic modification of the compound (II-a) thus-obtained may be resolved into each optical enantiomers thereof by using (S)-1-(2-naphthylsulfonyl)pyrrolidine-2-carbonyl chloride as a resolving agent, i.e., by the steps of reacting the compound (II-a) with said pyrrolidinecarbonyl chloride to give a pair of diastereoisomers, and then separating said diastereoisomers from each other by selective crystallization or by column chromatography. Hydrolysis of each diastereoisomers gives the optically active compound (II-a).

Alternatively, the compound (II) may be prepared by reacting a compound of the formula:

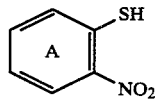
(IX)

wherein Ring A is the same as defined above, with the compound (VI), reducing the resultant compound of the formula:

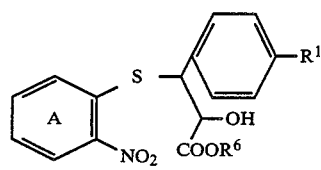
(X)

wherein $R^1$, $R^6$ and Ring A are the same as defined above, to give the compound (VII), and then treating said compound in the same manner as described in Step (III) to (VI) of the above-mentioned reaction scheme.

The reaction of the compound (IX) with the compound (VI) can be accomplished by heating a mixture of said compounds at 20° to 80° C. in a solvent (e.g., acetonitrile, toluene, benzene). The reduction of the compound (X) can be accomplished by reacting it with a reducing agent (e.g., stannous chloride in hydrochloric acid) at 0° to 50° C. in a solvent (e.g., acetic acid). The reduction of the compound (X) may be also accomplished by catalytic hydrogenation.

The compound (I) of the invention can be used for pharmaceutical use either as the free base or as an acid addition salt thereof. Pharmaceutically acceptable acid addition salts of the compound (I) are, for example, inorganic acid addition salts such as hydrochloride, hydrobromide, hydroiodide, perchlorate, sulfate or phosphate, organic acid addition salts such as oxalate, maleate, fumarate or methanesulfonate, and so forth. These salts may be prepared, for example, by neutralizing the compound (I) with an acid. The compound (I) or a pharmaceutically acceptable acid addition salt thereof may be administered either orally or parenterally. Further, the compound (I) or its salt may be used in the form of a pharmaceutical preparation containing the same compound in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparations may be in solid form such as tablets, pills, capsules or suppositories; or in liquid form such as solutions, suspensions or emulsions. Further, when administered parenterally, the pharmaceutical preparation may be used in the form of injections.

As mentioned hereinbefore, the compound (I) of the present invention has a potent hypotensive activity, a potent cerebral or coronary vasodilating activity and a potent platelet aggregation-inhibiting activity. Therefore, the compound (I) is useful for the treatment, amelioration or prophylaxis of hypertension; cerebral diseases such as cerebral vasospasm or cerebral infarction; and heart diseases such as angina pectoris, arrhythmias or coronary or cardiac infarction.

Therapeutic dose of the compound (I) or its salt depends on route of administration, the age, weight and conditions of patients; and particular diseases to be treated. In general, however, it may be used at a dose of 0.05 to 10 mg/kg/day, especially at a dose of 0.2 to 10 mg/kg/day in the case of oral administration or at a dose of 0.05 to 5 mg/kg/day in the case of parenteral administration (e.g., intravenous injection).

Practical and presently preferred embodiments of the present invention are illustratively shown in the following lines. Throughout the specification and claims, the term "lower alkyl", "lower alkoxy", "lower alkanoyl", "lower alkanoic acid anhydride" and "lower alkylthio" should be interpreted as referring to alkyl of one to 4 carbon atoms, alkoxy of one to 4 carbon atoms, alkanoyl of 2 to 4 carbon atoms, alkanoic acid anhydride of 4 to 8 carbon atoms and alkylthio of one to 4 carbon atoms, respectively.

Concomitantly, throughout the specification and claims, the term "threo" means that the hydroxy and substituted-phenylthio groups substituted at the 2- and 3-positions of propionic acid have threo-type configuration (i.e., said two groups are placed on opposite side of the central bond in the Fisher's projection formula).

EXPERIMENT 1

(Hypotensive activity)

A test compound (dose: 100 or 30 mg/kg) dissolved in water was administered orally to spontaneously hypertensive rats (SHR) (one group: 3 rats) fasted overnight. The systolic blood pressure of the rats was measured by the tail plethysmographic technique (The Journal of Laboratory and Clinical Medicine, 78 (1971), page 957). The hypotensive activity of the test compound was estimated one or 4 hours after dosing.

The results are shown in the following Table 1.

TABLE 1

| Test compound* Nos. | Dose (mg/kg) | Hypotensive activity Decrease in blood pressure (mm Hg) | |
|---|---|---|---|
| | | 1 hr | 4 hr |
| 1. | 100 | −78.9 | −104.7 |
| 2. | 100 | −119.8 | −110.2 |
| 3. | 100 | −109.6 | −109.9 |
| 4. | 30 | −114.0 | −94.0 |
| 5. | 30 | −75.3 | −80.7 |
| 6. | 30 | −92.3 | −75.0 |
| 7. | 30 | −63.7 | −50.0 |

Note: *:
Compound No. 1.
(±)-cis-2-(4-methoxyphenyl)-3-acetoxy-5-[2-(dimethylamino)ethyl]-7-methoxy-2,3-dihydro-1,5-benzothiazepin-4(5H)—one hydrochloride ½ H$_2$O
Compound No. 2.
(±)-cis-2-(4-methoxyphenyl)-3-acetoxy-5-[2-(dimethylamino)-ethyl]-7-methyl-2,3-dihydro-1,5-benzothiazepin-4(5H)—one hydrochloride
Compound No. 3.
(±)-cis-2-(4-methylphenyl)-3-acetoxy-5-[2-(dimethylamino)ethyl]-8-methoxy-2,3-dihydro-1,5-benzothiazepin-4(5H)—one oxalate
Compound No. 4.
(±)-cis-2-(4-methoxyphenyl)-3-acetoxy-5-[2-(dimethylamino)ethyl]-8-methoxy-2,3-dihydro-1,5-benzothiazepin-4(5H)—one hydrochloride ethanol
Compound No. 5.
(±)-cis-2-(4-methoxyphenyl)-3-acetoxy-5-[2-(dimethylamino)ethyl]-6-methoxy-2,3-dihydro-1,5-benzothiazepin-4(5H)—one oxalate ½ H$_2$O
Compound No. 6.
(±)-cis-2-(4-methoxyphenyl)-3-acetoxy-5-[2-(dimethylamino)ethyl]-7,8-dimethyl-2,3-dihydro-1,5-benzothiazepin-4(5H)—one hydrochloride
Compound No. 7.
(±)-cis-2-(4-methoxyphenyl)-3-acetoxy-5-[2-(dimethylamino)ethyl]-8-fluoro-2,3-dihydro-1,5-benzothiazepin-4(5H)—one hydrochloride ½ H$_2$O

EXPERIMENT 2

(Cerebral vasodilating activity)

Male dogs weighing 11–14 kg were anesthetized with sodium pentobarbital (30 mg/kg, intravenous injection). The blood flow in vertebral artery was measured continuously by means of an electromagnetic flowmeter under artificial respiration. A test compound was injected into vertebral artery. The cerebral vasodilating activity of the test compound was estimated in terms of the potency ratio of said compound to papaverine, which was calculated from the dose-response curves thereof. As a result, the cerebral vasodilating activities of (+)-cis-2-(4-methoxyphenyl)-3-acetoxy-5-[2-(dimethylamino)ethyl]-8-methyl-2,3-dihydro-1,5-benzothiazepin-4(5H)-one hydrobromide and (+)-cis-2-(4-methoxyphenyl)-3-acetoxy-5-[2-(dimethylamino)ethyl]-7-methyl-2,3-dihydro-1,5-benzothiazepin-4(5H)-one hydrobromide ¼ hydrate were about 12 times as strong as that of papaverine.

EXPERIMENT 3

(Coronary vasodilating activity)

Langendorff's method was used for testing the effect on the coronary blood flow of the isolated heart of guinea pig (about 280 g). The isolated heart was perfused with Lock-Riner solution (30° C.) containing 2% of defibrinated rabbit blood (said solution being saturated with a mixed gas of 95% O$_2$ and 5% CO$_2$). Perfusion pressure was kept at 40 cm H$_2$O. A solution of a test compound in an aqueous 5% glucose solution was injected into the perfusing solution at a volume of 0.1 ml per heart. The outflow of the persusate was measured by means of a drop counter.

The coronary vasodilating activity of the test compound was expressed as "±" if the increase in coronary blood flow is less than 0.5 ml/minute at a dose of 100 μg/heart; "+" if the increase is not less than 0.5 ml/minute at a dose of 100 μg/heart; "++" if the increase is not less than 0.5 ml/minute at a dose of 30 μg/heart; and "+++" if the increase is not less than 0.5 ml/minute at a dose of not more than 10 μg/heart.

The results are shown in the following Table 2.

TABLE 2

| Test compounds | Coronary vasodilating activity |
|---|---|
| (The compounds of the present invention) | |
| (±)-cis-2-(4-methoxyphenyl)-3-acetoxy-5-[2-(dimethylamino)ethyl]-6-methyl-2,3-dihydro-1,5-benzothiazepin-4(5H)—one hydrochloride | +++ |
| (±)-cis-2-(4-methoxyphenyl)-3-acetoxy-5-[2-(dimethylamino)ethyl]-8-methyl-2,3-dihydro-1,5-benzothiazepin-4(5H)—one hydrochloride ethanol | +++ |
| (+)-cis-2-(4-methoxyphenyl)-3-acetoxy-5-[2-(dimethylamino)ethyl]-8-methyl-2,3-dihydro-1,5-benzothiazepin-4(5H)—one hydrobromide | +++ |
| (±)-cis-2-(4-methoxyphenyl)-3-acetoxy-5-[2-(dimethylamino)ethyl]-6,7-dimethyl-2,3-dihydro-1,5-benzothiazepin-4(5H)—one hydrochloride 3/2 hydrate | +++ |
| (±)-cis-2-(4-methoxyphenyl)-3-hydroxy-5-[2-(dimethylamino)ethyl]-6,8-dimethyl-2,3-dihydro-1,5-benzothiazepin-4(5H)—one hydrochloride hydrate | +++ |
| (±)-cis-2-(4-methoxyphenyl)-3-acetoxy-5-[2-(dimethylamino)ethyl]-6,8-dimethyl-2,3-dihydro-1,5-benzothiazepin-4(5H)—one hydrochloride ethanol | +++ |
| (Positive control) | |
| Papaverine | + |

EXPERIMENT 4

(Platelet aggregation-inhibiting activity)

Blood was collected from the abdominal aorta of male Spraque-Dawley rats (body weight: 200–250 g) which were anesthetized with ether. Nine volumes of said blood were mixed with one volume of an aqueous 3.8% trisodium citrate solution, and the mixture was centrifuged at 250×g for 5 minutes to give platelet-rich plasma (hereinafter referred to as "PRP") as the supernatant solution. The bottom layer was further centrifuged at 750×g for 10 minutes to give platelet-poor plasma (hereinafter referred to as "PPP") as the supernatant solution. PRP was diluted with PPP so that the blood platelet count was 0.8×1×10$^6$/mm$^3$. Then, a mixture of 200 μl of said diluted PRP and 25 μl of a test compound solution (final concentration: 100 μg/ml) was introduced into a glass cell of an aggregometer. After the mixture was stirred for 2 minutes at 37° C., 25 μl of a collagen solution which was prepared by the method of Holmsen et al. [Biochem. Biophys. Acta, 186, page 254(1969)] were added thereto, and the percentage inhibition of platelet aggregation was calculated from the degree of platelet aggregation which was estimated by Born's method [Nature, 194, page 927(1962)]. Further, on the basis of said percentage inhibition calculated above, the platelet aggregation-inhibiting activity of the test compound was expressed as (−) if the test compound showed less than 10% inhibition of platelet aggregation; (+) if the test compound showed not less than 10% inhibition of platelet aggregation but said percentage inhibition was lower than that of acetylsalicylic acid (100 μg/ml); or (++) if the test compound showed the platele aggregation-inhibiting activity at least as strong as that of acetylsalicylic acid (100 μg/ml).

The results are shown in the following Table 3.

TABLE 3

| Test compounds | platelet aggregation-inhibiting activity |
|---|---|
| (±)-cis-2-(4-methoxyphenyl)-3-acetoxy-5-[2-(dimethylamino)ethyl]-8-methyl-2,3-dihydro-1,5-benzothiazepin-4(5H)—one hydrochloride ethanol | ++ |
| (±)-cis-2-(4-methoxyphenyl)-3-hydroxy-5-[2-(dimethylamino)ethyl]-8-methoxy-2,3-dihydro-1,5-benzothiazepin-4(5H)—one hydrochloride ethanol | ++ |
| (±)-cis-2-(4-methylphenyl)-3-acetoxy-5-[2-(dimethylamino)ethyl]-8-methyl-2,3-dihydro-1,5-benzothiazepin-4(5H)—one hydrochloride | ++ |
| (±)-cis-2-(4-methylphenyl)-3-acetoxy-5-[2-(dimethylamino)ethyl]-8-methoxy-2,3-dihydro-1,5-benzothiazepin-4(5H)—one oxalate | ++ |
| (±)-cis-2-(4-methoxyphenyl)-3-acetoxy-5-[2-(dimethylamino)ethyl]-7,8-dimethyl-2,3-dihydro-1,5-benzothiazepin-4(5H)—one hydrochloride | ++ |
| (±)-cis-2-(4-methoxyphenyl)-3-acetoxy-5-[2-(dimethylamino)ethyl]-8-fluoro-2,3-dihydro-1,5-benzothiazepin-4(5H)—one hydrochloride ¼ H₂O | ++ |

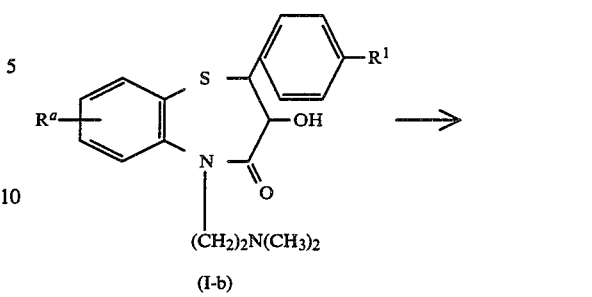

| Example Nos. | Compound (I-a) | | |
|---|---|---|---|
| | R¹ | Rᵃ | M.p., etc. |
| 2 | OCH₃ | 6-CH₃ | Hydrochloride: 208–210° C. (recrystallized from ethanol), Yield: 66% |
| 3 | CH₃ | 8-CH₃ | Hydrochloride: 184–186° C. (recrystallized from a mixture of isopropanol and ether), Yield: 86% |
| 4 | OCH₃ | 8-CH₃ | Hydrochloride-mono ethanol: 183.5–185.5° C. (recrystallized from ethanol), Yield: 79% |
| 5 | OCH₃ | 7-CH₃ | Hydrochloride: 157.5–159.5° C. (recrystallized from ethanol), Yield: 70% |

Note:
The compounds listed in the table are all (±)-cis isomers.

EXAMPLE 1

A mixture of 0.9 g of (±)-cis-2-(4-methylphenyl)-3-hydroxy-5-[2-(dimethylamino)ethyl]-8-methoxy-2,3-dihydro-1,5-benzothiazepin-4(5H)-one and 10 ml of acetic anhydride is stirred at 110° C. for 4 hours. After the reaction is completed, the mixture is evaporated under reduced pressure to remove acetic anhydride and acetic acid. Benzene is added to the residue, and the mixture is evaporated under reduced pressure to remove solvent. The residue is converted into its oxalate and then recrystallized from a mixture of chloroform, ethanol and ether. 1.15 g of (±)-cis-2-(4-methylphenyl)-3-acetoxy-5-[2-(dimethylamino)ethyl]-8-methoxy-2,3-dihydro-1,5-benzothiazepin-4(5H)-one oxalate are obtained. Yield 95%
M.p. 209°–211° C. (decomp)

EXAMPLE 2 TO 5

The following compounds are obtained in the same manner as described in Example 1.

EXAMPLE 6

A mixture of 1 g of (±)-cis-2-(4-methoxyphenyl)-3-hydroxy-5-[2-(dimethylamino)ethyl]-7-methoxy-2,3-dihydro-1,5-benzothiazepin-4(5H)-one hydrochloride, 1.5 ml of acetic anhydride and 1.5 ml of acetic acid is stirred at 110° C. for 4 hours. After the reaction is completed, the mixture is evaporated under reduced pressure to remove acetic anhydride and acetic acid. Benzene is added to the residue, and the mixture is evaporated under reduced pressure to remove acetic anhydride and acetic acid. The residue thus obtained is recrystallized from a mixture of ethanol and ether. 0.87 g of (±)-cis-2-(4-methoxyphenyl)-3-acetoxy-5-[2-(dimethylamino)ethyl]-7-methoxy-2,3-dihydro-1,5-benzothiazepin-4(5H)-one hydrochloride ½ hydrate is obtained. Yield: 78%
M.p. 216°–218° C.

EXAMPLE 7 TO 8

The following compounds are obtained in the same manner as described in Example 6.

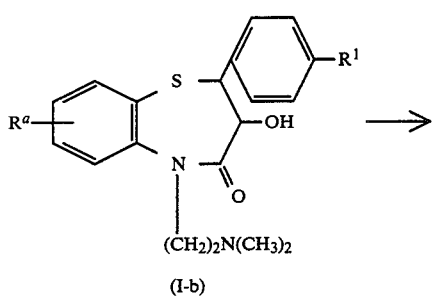

(I-b)

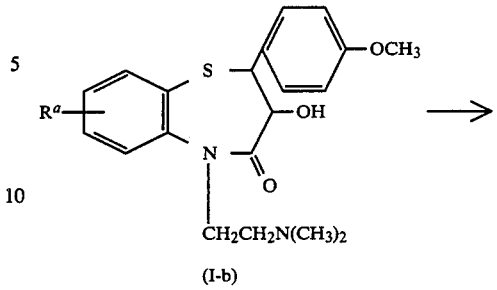

(I-b)

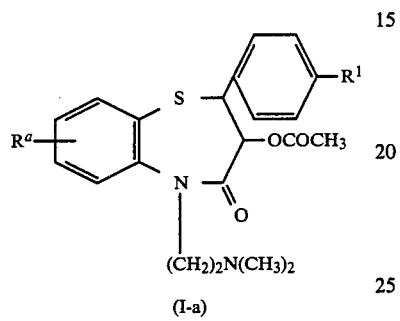

(I-a)

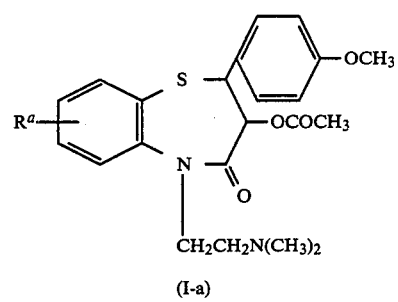

(I-a)

| Example Nos. | Compound (I-a) R¹ | Rª | M.p., etc. |
|---|---|---|---|
| 7 | $OCH_3$ | 8-$OCH_3$ | Hydrochloride-mono ethanol: 192–194° C. (recrystallized from a mixture of chloroform, ethanol and ether), Yield: 78% |
| 8 | $OCH_3$ | 6-$OCH_3$ | Oxalate-hemi hydrate: 212–213° C. (decomp., recrystallized from a mixture of ethanol, chloroform and ether), Yield: 82% |

Note:
The compounds listed in the Table are all (±)-cis isomers.

EXAMPLE 9

A mixture of 5.05 g of (±)-cis-2-(4-methoxyphenyl)-3-hydroxy-5-[2-(dimethylamino)ethyl]-8-methyl-2,3-dihydro-1,5-benzothiazepin-4(5H)-one, 20 ml of acetic anhydride and 0.1 ml of pyridine is stirred at 110° C. for 4 hours. After the reaction is completed, the mixture is evaporated under reduced pressure to remove acetic anhydride, acetic acid and pyridine. Benzene is added to the residue, and the mixture is evaporated under reduced pressure to remove solvent. The residue thus obtained is converted into its hydrobromide and recrystallized from a mixture of ethanol and ether. 6.374 g of (+)-cis-2-(4-methoxyphenyl)-3-acetoxy-5-[2-(dimethylamino)ethyl]-8-methyl-2,3-dihydro-1,5-benzothiazepin-4(5H)-one hydrobromide are obtained. Yield: 96%

M.p. 151°–152° C. (decomp)

$[\alpha]_D^{20} + 82.5°$ (c=0.308, methanol)

EXAMPLE 10 TO 17

The following compounds are obtained in the same manner as described in Example 9.

| Example Nos. | Compound (I-a) Rª | Optical isomer | M.p., etc. |
|---|---|---|---|
| 10 | 8-$OCH_2C_6H_5$ | ± | Hydrochloride-mono isopropanol: 171–174° C. (recrystallized from isopropanol), Yield: 75% |
| 11 | 8-$CH_3$ | — | Hydrobromide: 151–154° C. (decomp., recrystallized from a mixture of ethanol and ether), Yield: 94% $[\alpha]_D^{20} -82.1°$ (c = 0.42, methanol) |
| 12 | 7-$CH_3$ | + | Hydrobromide-¼ hydrate: 157–160° C. (recrystallized from a mixture of ethanol and ether), Yield: 97% $[\alpha]_D^{20} +87.8°$ (c = 0.303, methanol) |
| 13 | 7-$CH_3$ | — | Hydrobromide-¼ hydrate: 157–160° C. (recrystallized from a mixture of ethanol and ether), Yield: 95% $[\alpha]_D^{20} -88.7°$ (c = 0.549, methanol) |
| 14 | 8-$OCH_3$ | — | Hydrochloride: 164–166° C. (recrystallized from a mixture of ethanol and ether), Yield: 96%, $[\alpha]_D^{20} -79.9°$ (c = 0.344, methanol) |
| 15 | 8-$OCH_3$ | + | Hydrochloride: 164–166° C. (recrystallized from a mixture of ethanol and ether), Yield: 85%, $[\alpha]_D^{20} +79.4°$ (c = 0.389, methanol) |
| 16 | 8-$SCH_3$ | ± | Hydrochloride-mono ethanol: 179–182° C. (recrystallized from ethanol), Yield: 88% |
| 17 | 7-$SCH_3$ | ± | Hydrochloride-mono isopropanol: 198–200° C. (recrystallized from isopropanol), Yield: 76% |

Note:
The compounds listed in the Table are all cis isomers.

EXAMPLE 18

A mixture of 2.81 g of (±)-cis-2-(4-methoxyphenyl)-3-hydroxy-6-methyl-2,3-dihydro-1,5-benzothiazepin-4(5H)-one, 1.35 g of 2-(dimethylamino)ethyl chloride hydrochloride, 2.7 g of potassium carbonate and 40 ml of acetone is refluxed for 16 hours. After the reaction is completed, the inorganic materials are removed by filtration and then washed with chloroform. The filtrate and the washing are combined and then evaporated to remove solvent. The residue is converted into its hydrochloride and then recrystallized from a mixture of ethanol and ether. 2.93 g of (±)-cis-2-(4-methoxyphenyl)-3-hydroxy-5-[2-(dimethylamino)ethyl]-6-methyl-2,3-dihydro-1,5-benzothiazepin-4(5H)-one hydrochloride ¾ hydrate are obtained. Yield: 77%

M.p. 112°–115° C.

EXAMPLE 19 TO 33

The following compounds are obtained in the same manner as described in Example 18.

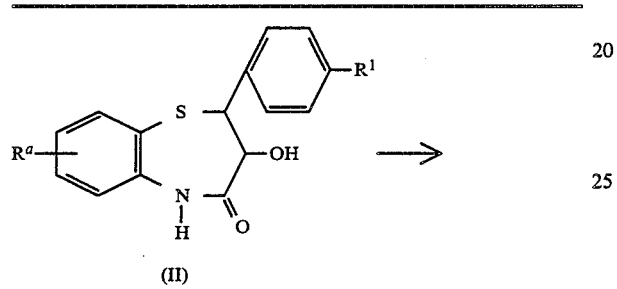

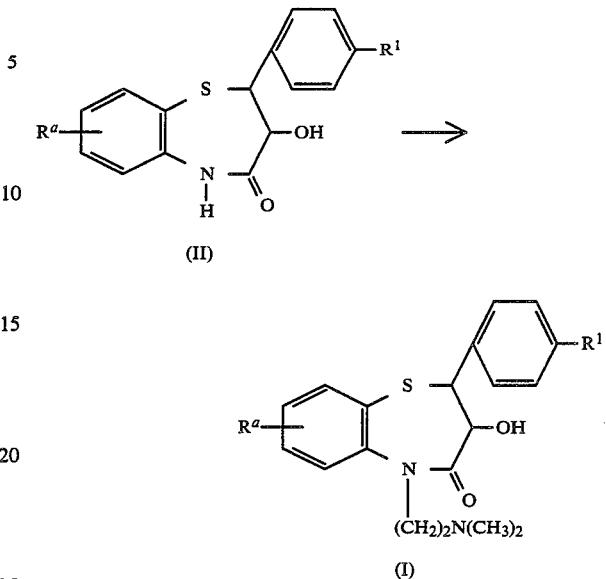

| Example Nos. | Compound (I) R$^1$ | R$^a$ | Optical isomer | M.p., etc. |
|---|---|---|---|---|
| 19 | CH$_3$ | 8-CH$_3$ | ± | Free base: 142–143° C. (recrystallized from ethyl acetate), Yield: 83% Hydrochloride: 168–169° C. (decomp., recrystallized from a mixture of ethanol and ether) |
| 20 | OCH$_3$ | 6-OCH$_3$ | ± | Hydrochloride: 199–202° C. (decomp. recrystallized from a mixture of ethanol and ether), Yield: 94% |
| 21 | CH$_3$ | 8-OCH$_3$ | ± | Free base: 127–130° C., Yield: 79% Hydrochloride-hemi hydrate: 153–155° C. (recrystallized from a mixture of ethanol and ether) |
| 22 | OCH$_3$ | 8-OCH$_2$C$_6$H$_5$ | ± | Hydrochloride-mono hydrate: 138–140° C. (recrystallized from a mixture of ethanol and ether, Yield: 81% |
| 23 | OCH$_3$ | 8-CH$_3$ | ± | Free base: 157–158° C. (recrystallized from ethyl acetate), Yield: 90% Hydrochloride: 232–234° C. (recrystallized from a mixture of ethanol and ether) |
| 24 | OCH$_3$ | 7-CH$_3$ | ± | Free base: 125–129° C. (recrystallized from ethyl acetate), Yield: 90% Hydrochloride: 235.5–236° C. (decomp., recrystallized from ethanol) |
| 25 | OCH$_3$ | 8-CH$_3$ | + | Free base: 120–122° C. (recrystallized from ethyl acetate), Yield: 96% $[\alpha]_D^{20}$ +155.0° (c = 0.465, methanol) |
| 26 | OCH$_3$ | 8-CH$_3$ | − | Free base: 121–123° C. (recrystallized from ethyl acetate), Yield: 96% $[\alpha]_D^{20}$ −153.1° (c = 0.40, methanol) |
| 27 | OCH$_3$ | 7-CH$_3$ | + | Free base: 94–95° C. (recrystallized from ethyl acetate), Yield: 93% $[\alpha]_D^{20}$ +159.8° (c = 0.43, methanol) |
| 28 | OCH$_3$ | 7-CH$_3$ | − | Free base: 94–95° C. (recrystallized from ethyl acetate), Yield: 92% $[\alpha]_D^{20}$ −160.8° (c = 0.325, methanol) |
| 29 | CH$_3$ | 8-OCH$_2$C$_6$H$_5$ | ± | Free base-hemi hydrate: 118–120° C. (recrystallized from a mixture of ethyl acetate and isopropyl ether), Yield: 91% |
| 30 | OCH$_3$ | 8-OCH$_3$ | + | Free base: 139–141° C. (recrystallized from ethyl acetate), Yield: 96% $[\alpha]_D^{20}$ +129.9° (c = 0.465, methanol) |
| 31 | OCH$_3$ | 8-OCH$_3$ | − | Free base: 139–141° C. (recrystallized from ethyl acetate), Yield: 93% $[\alpha]_D^{20}$ −127.8° (c = 0.385, methanol) |
| 32 | OCH$_3$ | 8-SCH$_3$ | ± | Free base: 153–154° C., Yield: 86% Hydrochloride: 247–251° C. (decomp., recrystallized from ethanol) |

-continued

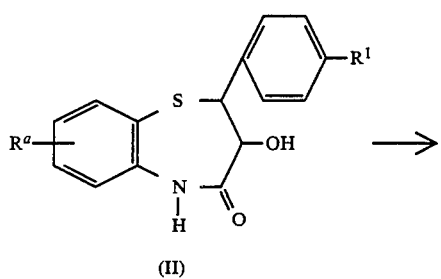

(II)

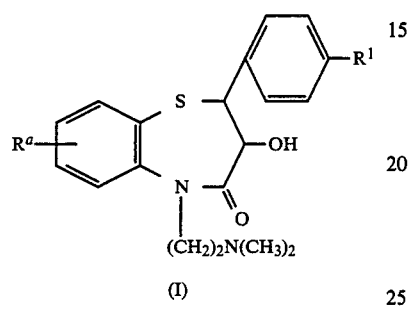

(I)

| Example Nos. | R¹ | Rᵃ | Optical isomer | M.p., etc. |
|---|---|---|---|---|
| 33 | OCH₃ | 7-SCH₃ | ± | Free base: 167–168° C., Yield: 70% Hydrochloride: 239–240° C. (decomp., recrystallized from ethanol) |

Note:
The compounds listed in the Table are all cis-isomers.

EXAMPLE 34

A mixture of 0.828 g of (±)-cis-2-(4-methoxyphenyl)-3-hydroxy-7-methoxy-2,3-dihydro-1,5-benzothiazepin-4(5H)-one, 0.307 g of potassium hydroxide and 15 ml of dimethylsulfoxide is stirred at room temperature for 2 hours, and then 0.396 g of 2-(dimethylamino)ethyl chloride hydrochloride is added thereto. The mixture is stirred at room temperature for 16 hours. After the reaction is completed, the mixture is poured into ice-water, and the aqueous solution is extracted with ethyl acetate. The ethyl acetate solution is extracted with a 10% hydrochloric acid solution. The extract is adjusted to about pH 10 with potassium carbonate. The alkaline solution is extracted witn ethyl acetate, and the extract is washed with water, dried and then evaporated to remove solvent. The residue is recrystallized from a mixture of ethyl acetate and n-hexane. 0.82 g of (±)-cis-2-(4-methoxyphenyl)-3-hydroxy-5-[2-(dimethylamino)ethyl]-7-methoxy-2,3-dihydro-1,5-benzothiazepin-4(5H)-one is obtained. Yield: 82%

M.p. 127°–129° C.

Hydrochloride: M.p. 212°–214° C. (recrystallized from a mixture of chloroform, ethanol and ether)

EXAMPLE 35

The following compound is obtained in the same manner as described in Example 34.

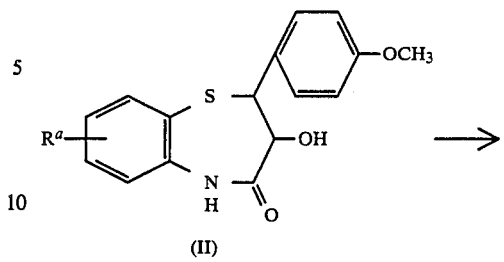

(II)

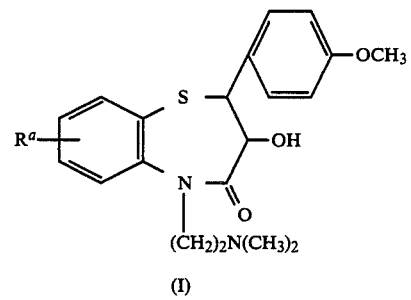

(I)

| Example Nos. | Rᵃ | Optical isomer | M.p., etc. |
|---|---|---|---|
| 35 | 8-OCH₃ | ± | Hydrochloride-mono ethanol: 130–132° C. (recrystallized from a mixture of chloroform, ethanol and ether), Yield: 77% |

Note:
The compound listed in the Table is cis-isomer.

EXAMPLE 36

A mixture of one g of (±)-cis-2-(4-methoxyphenyl)-3-hydroxy-5-[2-(dimethylamino)ethyl]-7,8-dimethyl-2,3-dihydro-1,5-benzothiazepin-4(5H)-one and 10 ml of acetic anhydride is stirred at 110° C. for 4 hours. After the reaction is completed, the mixture is evaporated under reduced pressure to remove acetic anhydride and acetic acid. Benzene is added to the residue, and the mixture is evaporated under reduced pressure to remove solvent. The residue is converted to its hydrochloride and then recrystallized from a mixture of chloroform, ethanol and ether. 1.15 g of (±)-cis-2-(4-methoxyphenyl)-3-acetoxy-5-[2-(dimethylamino)ethyl]-7,8-dimethyl-2,3-dihydro-1,5-benzothiazepin-4(5H)-one hydrochloride are obtained.

M.p. 209°–211° C. (decomp.)

EXAMPLE 37

A mixture of 4.75 g of (+)-cis-2-(4-methoxyphenyl)-3-hydroxy-5-[2-(dimethylamino)ethyl]-7,8-dimethyl-2,3-dihydro-1,5-benzothiazepin-4(5H)-one, 50 ml of acetic anhydride and one ml of pyridine is heated at 110° C. for 4 hours. After the reaction is completed, the mixture is evaporated under reduced pressure to remove acetic anhydride, acetic acid and pyridine. Benzene is added to the residue, and the mixture is evaporated under reduced pressure. The residue is converted to its oxalate and then recrystallized from a mixture of chloroform and ethanol. 5.37 g of (+)-cis-2-(4-methoxyphenyl)-3-acetoxy-5-[2-(dimethylamino)ethyl]-7,8-dimethyl-2,3-dihydro-1,5-benzothiazepin-4(5H)-one oxalate ½ H₂O are obtained.

M.p. 191°–192° C. (decomp.)

$[\alpha]_D^{20} + 101.9°$ (C=0.736, dimethylformamide)

EXAMPLE 38 TO 41

The following compounds are obtained in the same manner as described in Example 37.

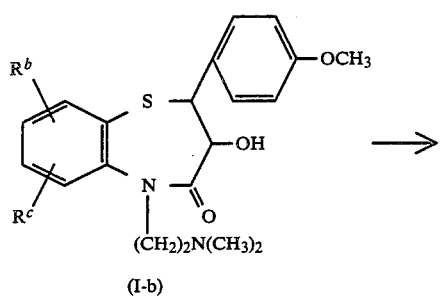

(I-b)

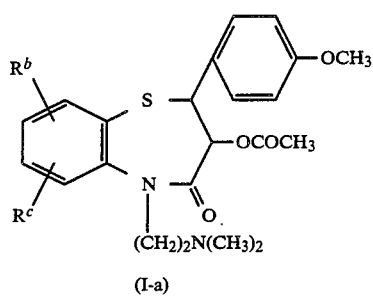

(I-a)

| Example Nos. | $R^b$, $R^c$ | Optical isomer | M.p., etc. |
|---|---|---|---|
| 38 | 7,8-$(CH_3)_2$ | — | Oxalate hemihydrate; 189–191° C. (decomp., recrystallized from a mixture of chloroform and ethanol) $[\alpha]_D^{20} -99.5°$ (c = 0.79, dimethylformamide), Yield: 82.4% |
| 39 | 7,8-$(OCH_3)_2$ | ± | Hydrochloride: 241.5–243° C. (decomp., recrystallized from ethanol), Yield: 89.4% |
| 40 | 7,8-$Cl_2$ | ± | Hydrochloride: 189–192° C. (recrystallized from methanol) (turbid melt at 182° C.), Yield: 85.3% |
| 41 | 8,9-$Cl_2$ | ± | Hydrochloride hemihydrate: 233–235° C. (decomp., recrystallized from a mixture of methanol and ether), Yield: 85.1% |

Note:
The compounds listed in the Table are all cis-isomers.

EXAMPLE 42

A mixture of 0.618 g of (±)-cis-2-(4-methoxyphenyl)-3-hydroxy-5-[2-(dimethylamino)ethyl]-6,7-dimethyl-2,3-dihydro-1,5-benzothiazepin-4(5H)-one hydrochloride, 6 ml of acetic anhydride and 6 ml of acetic acid is heated at 105° C. for 18 hours. After the reaction is completed, the mixture is evaporated under reduced pressure to remove solvent. Benzene is added to the residue, and the mixture is evaporated under reduced pressure to remove solvent. The residue is recystallized from a mixture of ethanol and ether. 0.44 g of (±)-cis-2-(4-methoxyphenyl)-3-acetoxy-5-[2-(dimethylamino)ethyl]-6,7-dimethyl-2,3-dihydro-1,5-benzothiazepin-4(5H)-one hydrochloride 3/2 $H_2O$ is obtained.

M.p. 245° C. (decomp.), (turbid metl at 150°–152° C.)

EXAMPLE 43 TO 44

The following compounds are obtained in the same manner as described in Example 42.

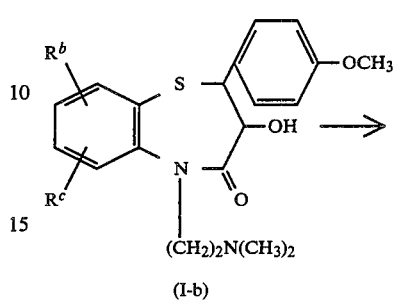

(I-b)

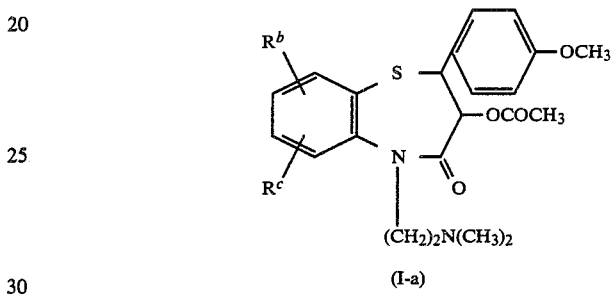

(I-a)

| Example Nos. | $R^b$, $R^c$ | M.p., etc. |
|---|---|---|
| 43 | 6,8-$(CH_3)_2$ | Hydrochloride mono-ethanol: 218–221° C. (recrystallized from a mixture of ethanol and ether), Yield: 77.4% |
| 44 | 7,9-$(CH_3)_2$ | Hydrochloride: 240–242° C. (decomp., recrystallized from a mixture of ethanol and ether), Yield: 86% |

Note:
The compounds listed in the Table are all (±)-cis isomers.

EXAMPLE 45

A mixture of 8.2 g of (±)-cis-2-(4-methoxyphenyl)-3-hydroxy-7,8-dimethyl-2,3-dihydro-1,5-benzothiazepin-4(5H)-one, 3.1 g of potassium hydroxide and 100 ml of dimethylsulfoxide is stirred at room temperature for 30 minutes. Then, 4 g of 2-(dimethylamino)ethyl chloride hydrochloride are added to the mixture, and said mixture is stirred at room temperature for 20 hours. After the reaction is completed, the mixture is poured into ice-water. The aqueous mixture is extracted with ethyl acetate, and the ethyl acetate layer is further extracted with 20% hydrochloric acid. The hydrochloric acid layer is alkalized with conc. aqueous ammonia, and the precipitated crystals are collected by filtration, washed with water and then dried. 6.4 g of (±)-cis-2-(4-methoxyphenyl)-3-hydroxy-5-[2-(dimethylamino)ethyl]-7,8-dimethyl-2,3-dihydro-1,5-benzothiazepin-4(5H)-one are obtained.

M.p. 179°–181° C.

Hydrochloride: M.p. 248°–250° C. (decomp.) (recrystallized from a mixture of chloroform, ethanol and ether)

EXAMPLE 46

A mixture of 4.4 g of (+)-cis-2-(4-methoxyphenyl)-3-hydroxy-7,8-dimethyl-2,3-dihydro-1,5-benzothiazepin-4(5H)-one, 2.12 g of 2-(dimethylamino)ethyl chloride hydrochloride, 4.06 g of potassium carbonate and 200 ml of acetone is refluxed for 20 hours. After the reaction is completed, insoluble materials are removed by filtration and then washed with ethanol. The filtrate and the washing are combined and then evaporated to remove solvent. The residue is dissolved in ethyl acetate, and the solution is washed with water, dried and then evaporated to remove solvent. The residue is recrystallized from a mixture of ethyl acetate and n-hexane. 4.85 g of (+)-cis-2-(4-methoxyphenyl)-3-hydroxy-5-[2-(dimethylamino)ethyl]-7,8-dimethyl-2,3-dihydro-1,5-benzothiazepin-4(5H)-one are obtained.

M.p. 117°–118° C.

$[\alpha]_D^{20} + 149.7°$ (C=0.68, methanol)

EXAMPLE 47 TO 51

The following compounds are obtained in the same manner as described in Example 46.

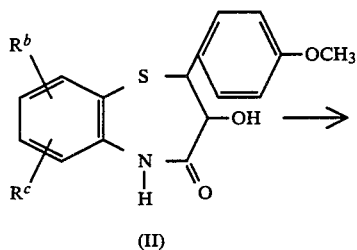

(II)

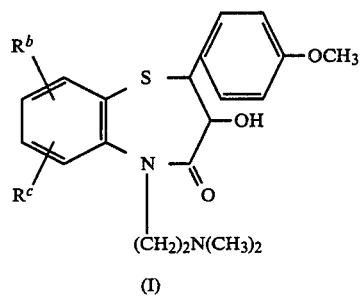

(I)

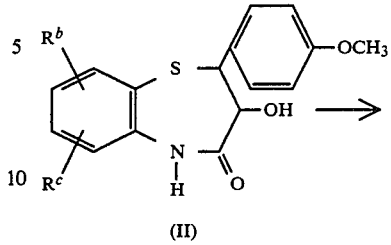

(II)

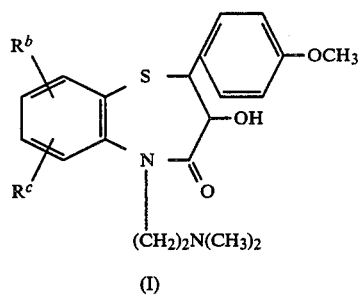

(I)

| Example Nos. | $R^b$, $R^c$ | Optical isomer | Compound (I) M.p., etc. |
|---|---|---|---|
| 47 | 7,8-(CH$_3$)$_2$ | — | Free base: 117–119° C. (recrystallized from a mixture of ethyl acetate and n-hexane) $[\alpha]_D^{20}$ −141.1° (c=0.792, methanol) Yield: 84% |
| 48 | 7,8-(OCH$_3$)$_2$ | ± | Free base: 154.5–156° C. (recrystallized from methanol) Yield: 75.6% Oxalate monohydrate: 192–194° C. (decomp., recrystallized from methanol) |
| 49 | 6,7-(CH$_3$)$_2$ | ± | Hydrochloride monohydrate: 117–119° C. (decomp., recrystallized from a mixture of ethanol and ether), Yield: 80% |
| 50 | 6,8-(CH$_3$)$_2$ | ± | Hydrochloride monohydrate: 124–148° C. (decomp., recrystallized from ethanol) (turbid melt at 119° C.), Yield: 81.6% |
| 51 | 7,9-(CH$_3$)$_2$ | ± | Hydrochloride: 224–225° C. (decomp., recrystallized from a mixture of ethanol and ether) (turbid melt at 145° C.) Yield: 86.5% |

Note:
The compounds listed in the Table are all cis-isomers.

EXAMPLE 52

A mixture of 1.48 g of (±)-cis-2-(4-methoxyphenyl)-3-hydroxy-7,8-dichloro-2,3-dihydro-1,5-benzothiazepin-4(5H)-one, 0.64 g of 2-(dimethylamino)ethyl chloride hydrochloride, 1.66 g of potassium carbonate, 45 ml of acetone and 0.5 ml of water is refluxed for 22 hours. After the reaction is completed, insoluble materials are removed by filtration. The filtrate is evaporated to remove solvent, and diisopropyl ether is added to the residue. The precipitated crystals are collected by filtration and then recrystallized from ethyl acetate. 1.18 g of (±)-cis-2-(4-methoxyphenyl)-3-hydroxy-5-[2-(dimethylamino)ethyl]-7,8-dichloro-2,3-dihydro-1,5-benzothiazepin-4(5H)-one are obtained.

M.p. 178°–179.5° C.

Hydrochloride:

M.p. 232.5°–234° C. (decomp.) (recrystallized from methanol)

EXAMPLE 53

The following compound is obtained in the same manner as described in Example 52.

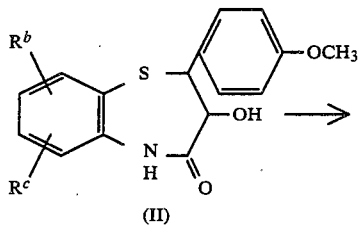

(II)

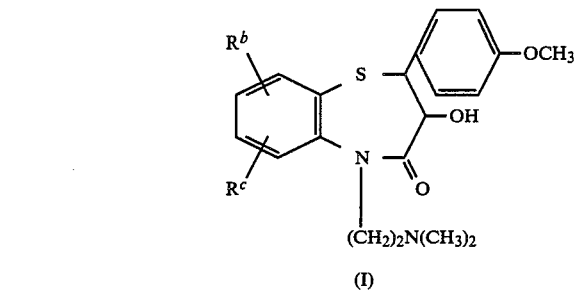

(I)

| Example Nos. | Compound (I) $R^b$, $R^c$ | M.p., etc. |
|---|---|---|
| 53 | 8,9-$Cl_2$ | Free base: 175.5–176.5° C. (recrystallized from ethyl acetate), Yield: 46% Hydrochloride 3/2 hydrate: 172–175° C. (recrystallized from a mixture of methanol and ether) [230–233° (decomp.) (turbid melt at 156° C.)] |

Note:
The compound listed in the Table is (±)-cis isomer.

EXAMPLE 54

A mixture of 0.7 g of (±)-cis-2-(4-methoxyphenyl)-3-hydroxy-5-[2-(dimethylamino)ethyl]-8-fluoro-2,3-dihydro-1,5-benzothiazepin-4(5H)-one hydrochloride and 8 ml of acetic anhydride is heated at 100° C. for 4 hours. After the reaction is completed, the mixture is evaporated under reduced pressure to remove acetic anhydride and acetic acid. Toluene is added to the residue, and the mixture is evaporated under reduced pressure to remove solvent. The residue is recrystallized from a mixture of ethanol and ether. 0.68 g of (±)-cis-2-(4-methoxyphenyl)-3-acetoxy-5-[2-(dimethylamino)ethyl]-8-fluoro-2,3-dihydro-1,5-benzothiazepin-4(5H)-one hydrochloride $\frac{1}{2}H_2O$ is obtained.
M.p. 137°–141° C.

EXAMPLE 55

A mixture of 1 g of (±)-cis-2-(4-methoxyphenyl)-3-hydroxy-5-[2-(dimethylamino)ethyl]-9-fluoro-2,3-dihydro-1,5-benzothiazepin-4(5H)-one and 10 ml of acetic anhydride is treated in the same manner as described in Example 54. The crude product is converted to its hydrochloride and recrystallized from a mixture of isopropanol and ether. 0.729 g of (±)-cis-2-(4-methoxyphenyl)-3-acetoxy-5-[2-(dimethylamino)ethyl]-9-fluoro-2,3-dihydro-1,5-benzothiazepin-4(5H)-one hydrochloride is obtained.
M.p. 200°–204° C. (decomp.) (turbid melt at 194° C.)

EXAMPLE 56

A mixture of 4 g of (±)-cis-2-(4-methoxyphenyl)-3-hydroxy-8-fluoro-2,3-dihydro-1,5-benzothiazepin-4(5H)-one, 1.99 g of 2-(dimethylamino)ethyl chloride hydrochloride, 4.3 g of potassium carbonate and 50 ml of acetone is refluxed for 18 hours. After the reaction is completed, insoluble materials are removed by filtration and washed with hot acetone. The filtrate and the washings are combined and then evaporated to remove solvent. The residue is converted to its hydrochloride and recrystallized from a mixture of isopropanol, ethanol and ether. 4 g of (±)-cis-2-(4-methoxyphenyl)-3-hydroxy-5-[2-(dimethylamino)ethyl]-8-fluoro-2,3-dihydro-1,5-benzothiazepin-4(5H)-one hydrochloride are obtained.
M.p. 197°–198° C.

EXAMPLE 57

A mixture of 1.2 g of (±)-cis-2-(4-methoxyphenyl)-3-hydroxy-9-fluoro-2,3-dihydro-1,5-benzothiazepin-4(5H)-one, 0.65 g of 2-(dimethylamino)ethyl chloride hydrochloride, 1.3 g of potassium carbonate and 50 ml of acetone is treated in the same manner as described in Example 56. The crude product thus obtained is converted to its hydrochloride and recrystallized from isopropanol. 1.7 g of (±)-cis-2-(4-methoxyphenyl)-3-hydroxy-5-[2-(dimethylamino)ethyl-]-9-fluoro-2,3-dihydro-1,5-benzothiazepin-4(5H)-one hydrochloride are obtained.
M.p. 202°–205° C. (turbid melt at 198° C.)

EXAMPLE 58

A mixture of 406 mg of (±)-cis-2-(4-methoxyphenyl)-3-acetoxy-8-methoxy-1,5-benzothiazepin-4(5H)-one, 170 mg of 2-(dimethylamino)ethyl chloride hydrochloride, 370 mg of potassium carbonate and 30 ml of acetone is refluxed for 20 hours. After the reaction is completed, insoluble materials are removed by filtration and washed with hot acetone. The filtrate and the washings are combined and then evaporated under reduced pressure to remove solvent. The residue is converted to its hydrochloride and recrystallized from a mixture of chloroform, ethanol and ether. 440 mg of (±)-cis-2-(4-methoxyphenyl)-3-acetoxy-5-[2-(dimethylamino)ethyl]-8-methoxy-2,3-dihydro-1,5-benzothiazepin-4(5H)-one hydrochloride ethanol are obtained.
M.p. 192°–194° C.

EXAMPLE 59

A mixture of 190 mg of (±)-cis-2-(4-methoxyphenyl)-3-acetoxy-7,8-dimethyl-2,3-dihydro-1,5-benzothiazepin-4(5H)-one, 81 mg of 2-(dimethylamino)ethyl chloride hydrochloride, 180 mg of potassium carbonate and 15 ml of acetone is treated in the same manner as described in Example 58. The crude product is converted to its hydrochloride and recrystallized from a mixture of chloroform, ethanol and ether. 177 mg of (±)-cis-2-(4-methoxyphenyl)-3-acetoxy-5-[2-(dimethylamino)ethyl]-7,8-dimethyl-2,3-dihydro-1,5-benothiazepin-4(5H)-one hydrochloride are obtained.
M.p. 209°–211° C. (decomp.)

(Preparation of the starting compounds)

PREPARATION 1

A mixture of 13 g of 2-amino-4-methoxy-thiophenol and 17.6 g of methyl (±)-trans-3-(4-methoxyphenyl)-glycidate is heated at 160° C. for 16 hours under argon atmosphere. After cooling, ethanol is added to the mixture. The precipitated crystals are collected by filtration and recrystallized from chloroform. 4.52 g of (±)-cis-2-

(4-methoxyphenyl)-3-hydroxy-7-methoxy-2,3-dihydro-1,5-benzothiazepin-4(5H)-one are obtained.

M.p. 220°–222° C.

The mother liquors (The ethanol and chloroform solutions) are combined and evaporated to remove solvent. The residue is purified by silica gel chromatography (Solvent: chloroform). 2.9 g of (±)-cis-2-(4-methoxyphenyl)-3-hydroxy-7-methoxy-2,3-dihydro-1,5-benzothiazepin-4(5H)-one and 1.1 g of (±)-trans-2-(4-methoxyphenyl)-3-hydroxy-7-methoxy-2,3-dihydro-1,5-benzothiazepin-4(5)-one are further obtained from the eluates. (±)-Trans-isomer:

M.p. 189°–190° C. (recrystallized from a mixture of ethyl acetate and n-hexane)

PREPARATION 2 TO 10

The following compounds are obtained from the corresponding starting materials in the same manner as described in Preparation 1.

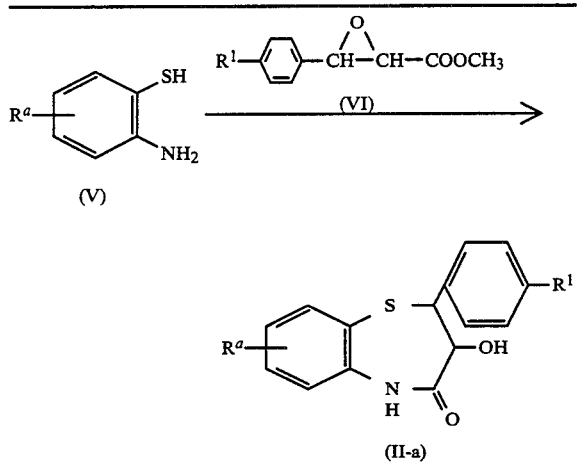

| Preparation Nos. | R¹ | Rᵃ | Compound (II-a) M.p., etc. |
|---|---|---|---|
| 2 | OCH₃ | 8-OCH₃ | Cis-isomer: 204–206° C. (recrystallized from ethyl acetate) Trans-isomer: 150–152° C. (recrystallized from a mixture of ethyl acetate and n-hexane) |
| 3* | OCH₃ | 6-CH₃ | Cis-isomer: 225–227.5° C. (recrystallized from a mixture of dimethylformamide and ethanol) Trans-isomer: 231–233° C. (recrystallized from a mixture of dimethylformamide and ethanol) |
| 4 | CH₃ | 8-CH₃ | Cis-isomer: 182.5–184.5° C. (recrystallized from a mixture of dimethylformamide and ethanol) |
| 5 | OCH₃ | 6-OCH₃ | Cis-isomer-hemi hydrate: 208–210° C. (recrystallized from a mixture of chloroform and n-hexane) |
| 6 | CH₃ | 8-OCH₃ | Cis-isomer: 202–206° C. (recrystallized from ethanol) Trans-isomer: 185–188° C.) (recrystallized from ethanol) |
| 7 | OCH₃ | 8-OCH₂C₆H₅ | Cis-isomer: 172–174° C. (recrystallized from a mixture of dimethylformamide and ethanol) |
| 8 | OCH₃ | 8-CH₃ | Cis-isomer: 219–221° C. (recrystallized from dimethylformamide) |
| 9 | OCH₃ | 7-CH₃ | Cis-isomer: 218–221° C. (recrystallized from dimethylformamide) |

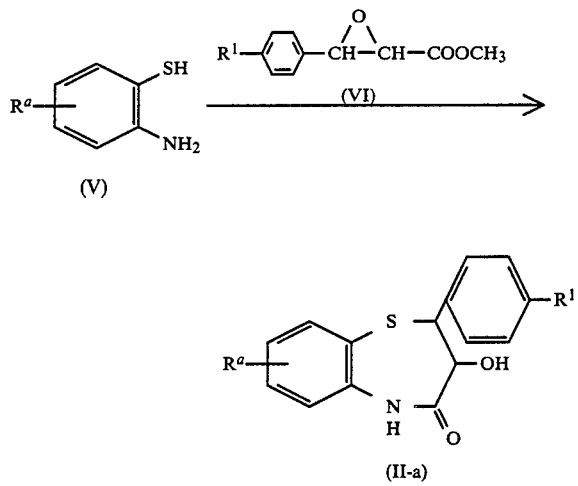

| Preparation Nos. | R¹ | Rᵃ | Compound (II-a) M.p., etc. |
|---|---|---|---|
| 10 | CH₃ | 8-OCH₂C₆H₅ | Cis-isomer: 164–165° C. (recrystallized from ethanol) |

Note:
The compounds listed in the Table are all racemic compounds.

*Methyl (±)-threo-2-hydroxy-3-(4-methoxyphenyl)-3-(2-amino-3-methylphenylthio)propionate is obtained in addition to the compounds listed above. M.p. 98–110° C. (recrystallized from ethanol)

PREPARATION 11

(a) A mixture of 29.1 g of 2-amino-5-methyl-thiophenol, 47.8 g of methyl (±)-trans-3-(4-methoxyphenyl)glycidate and 300 ml of toluene is heated at 60°–65° C. for 3 days and then at 70°–80° C. for 2 days. The mixture is evaporated under reduced pressure to remove solvent. Benzene is added to the residue and the mixture is extracted with conc. hydrochloric acid-water (1:1). The extract is neutralized with potassium carbonate, and the aqueous solution is extracted with benzene. The extract is washed with water, dried and then evaporated to remove benzene. The residue is chromatographed on silica gel (Solvent: benzene-ethyl acetate=10:1). The crude product thus obtained is recrystallized from a mixture of ethanol and isopropyl ether. 15.8 g of methyl (±)-threo-2-hydroxy-3-(2-amino-5-methylphenylthio)-3-(4-methoxyphenyl)propionate are obtained.

M.p. 110°–112° C.

The following compounds are obtained from the corresponding starting materials in the same manner as above.

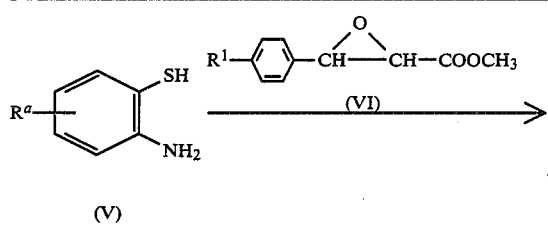

(V)

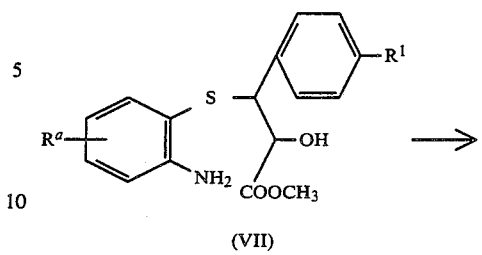

(VII)

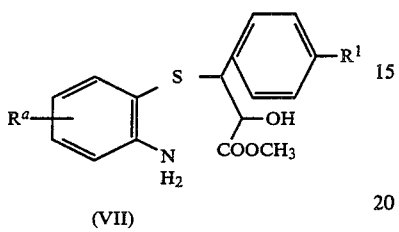

(VII)

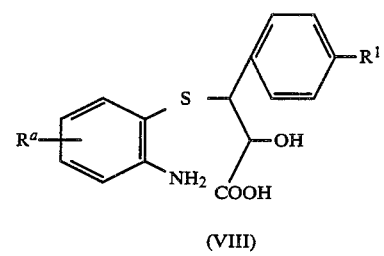

(VIII)

Compound (VII)

| Nos. | R¹ | Rᵃ | Reaction conditions | M.p., etc. |
|---|---|---|---|---|
| i | OCH₃ | 4-CH₃ | 60–70° C., 4 days | 107–108° C. (recrystallized from ethanol-isopropyl ether) |
| ii | CH₃ | 5-CH₃ | 60° C., 4 days + 100° C., 8 days | 114–114.5° C. (recrystallized from isopropyl ether) |
| iii* | OCH₃ | 5-SCH₃ | 90° C., 20 hours | 114–116° C. (recrystallized from ethanol) |
| iv | OCH₃ | 4-SCH₃ | 90° C., 20 hours | 130–132° C. (recrystallized from ethanol) |
| v | OCH₃ | 5-OCH₃ | 70–75° C., 5 days | 99.5–102.5° C. (recrystallized from isopropanol) |

Note:
The compounds listed in the Table are all (±)-threo isomers.
*(±)-Cis-2-(4-methoxyphenyl)-3-hydroxy-8-methylthio-2,3-dihydro-1,5-benzothiazepin-4(5H)-one is obtained in addition to the compound listed above.
M.p. 183–184° C. (recrystallized from a mixture of dimethylformamide and ethanol)

(b) A mixture of 5 g of methyl (±)-threo-2-hydroxy-3-(2-amino-5-methylphenylthio)-3-(4-methoxyphenyl)-propionate, 50 ml of an aqueous 5% sodium hydroxide solution and 50 ml of methanol is stirred at room temperature for 2 hours. After the reaction is completed, the mixture is adjusted to pH 3 to 5 with 10% hydrochloric acid under ice-cooling. The precipitated crystals are collected by filtration, washed with water, dried and then recrystallized from methanol. 4.3 g of (±)-threo-2-hydroxy-3-(2-amino-5-methylphenylthio)-3-(4-methoxyphenyl)propionic acid are obtained.

M.p. 190°–193° C.

The following compounds are obtained from the corresponding starting materials in the same manner as above.

Compound (VIII)

| Nos. | R¹ | Rᵃ | Solvent | M.p., etc. |
|---|---|---|---|---|
| i | OCH₃ | 4-CH₃ | Methanol | 168–170° C. (recyrstallized from methanol) |
| ii | CH₃ | 5-CH₃ | Ethanol | 168–172° C. |
| iii | OCH₃ | 5-OCH₃ | Ethanol | 210–212° C. (decomp.) |

Note:
The compounds listed in the Table are all (±)-threo isomers.

(c) 45.3 g L-(p-hydroxyphenyl)glycine methyl ester hydrochloride are dissolved in 1000 ml of methanol. A solution of 11.7 g of potassium hydroxide in 100 ml of methanol is added to the solution under ice-cooling, and the precipitates (potassium chloride) are removed by filtration. 37.8 g of of (±)-threo-2-hydroxy-3-(2-amino-5-methylphenylthio)-3-(4-methoxyphenyl)propionic acid are added to the filtrate. The mixture is warmed to about 50° C., and then 900 ml of methanol are added thereto to make a clear solution. The clear solution is evaporated under reduced pressure at a temperature of below 50° C. 200 ml of ethanol are added to the residue, and the mixture is allowed to stand in a refrigerator overnight. The precipitated crystals are collected by filtration (The mother liquor is referred as "Mother liquor I".), and then recrystallized from ethanol (The mother liquor is referred to "Mother liquor II".). The crude products thus obtained is further recrystallized from ethanol. 20.7 g of (±)-threo-2-hydroxy-3-(2-amino-5-methylphenylthio)-3-(4-methoxyphenyl)propionic acid.L-(p-hydroxyphenyl)glycine methyl ester salt (M.p. 164°–167° C. $[\alpha]_D^{20}+255.8°$ (c=0.655, methanol)) are obtained.

15.3 g of the product thus obtained are suspended in a mixture of 240 ml of methanol and 200 ml of water, and 27 ml of cation exchange resins are added thereto. The mixture is stirred at room temperature overnight. The resins are removed by filtration and washed with methanol. The filtrate and the washing are combined and evaporated under reduced pressure to remove solvent. Water is added to the residue. The precipitated crystals are collected by filtration and then recrystallized from ethanol. 7 g of (+)-threo-2-hydroxy-3-(2-amino-5-methylphenylthio)-3-(4-methoxyphenyl)propionic acid are obtained.

M.p. 158°–160° C.

$[\alpha]_D^{20} +296.0°$ (c=0.290, methanol)

Mother liquors I and II are combined, and 13 ml of conc. hydrochloric acid are added thereto. The mixture is evaporated under reduced pressure to remove solvent. Water is added to the residue, and the precipitated crystals are collected by filtratin. Then, the crystals (15.5 g) thus obtained, 20.3 g of D-(p-hydroxyphenyl)glycine methyl ester hydrochloride and 5.2 g of potassium hydroxide are treated in the same manner as above. 12.9 g of (−)-threo-2-hydroxy-3-(2-amino-5-methylphenylthio)-3-(4-methoxyphenyl)propionic acid.D-(p-hydroxyphenyl)glycine methyl ester salt (M.p. 164°-167° C. (recrystallized from ethanol, $[\alpha]_D^{20} -254.8°$ (c=0.949, methanol)) are obtained.

The product (15.3 g) thus obtained are then converted into its free acid in the same manner as above. 6.5 g of (−)-threo-2-hydroxy-3-(2-amino-5-methylphenylthio)-3-(4-methoxyphenyl)propionic acid are obtained.

M.p. 158°-160° C. (recrystallized from ethanol)

$[\alpha]_D^{20} -265.3°$ (c=0.331, methanol)

The following compounds are obtained from (±)-threo-2-hydroxy-3-(2-amino-4-methylphenylthio)-3-(4-methoxyphenyl)propionic acid in the same manner as above.

(+)-Threo-2-hydroxy-3-(2-amino-4-methylphenyl-thio)-3-(4-methoxyphenyl)propionic acid:

M.p. 168°-170° C. (recrystallized from ethanol)

$[\alpha]_D^{20} +360.3°$ (c=0.342, methanol)

(−)-Threo-2-hydroxy-3-(2-amino-4-methylphenyl-thio)-3-(4-methoxyphenyl)propionic acid:

M.p. 173°-176° C. (recrystallized from ethanol)

$[\alpha]_D^{20} -360.5°$ (c=0.352, methanol)

(d) A mixture of 9 g of (+)-threo-2-hydroxy-3-(2-amino-5-methylphenylthio)-3-(4-methoxyphenyl)propionic acid and 350 ml of xylene is refluxed for 24 hours. The resulting water is removed during the reaction. After the reaction, the mixture is evaporated to remove xylene, and the residue is recrystallized from ethyl acetate. 7.8 g of (+)-cis-2-(4-methoxyphenyl)-3-hydroxy-8-methyl-2,3-dihydro-1,5-benzothiazepin-4(5H)-one are obtained.

M.p. 223°-226° C. (decomp.)

$[\alpha]_D^{20} +123.8°$ (c=0.707, dimethylformamide)

The following compounds are obtained from the corresponding starting materials in the same manner as above.

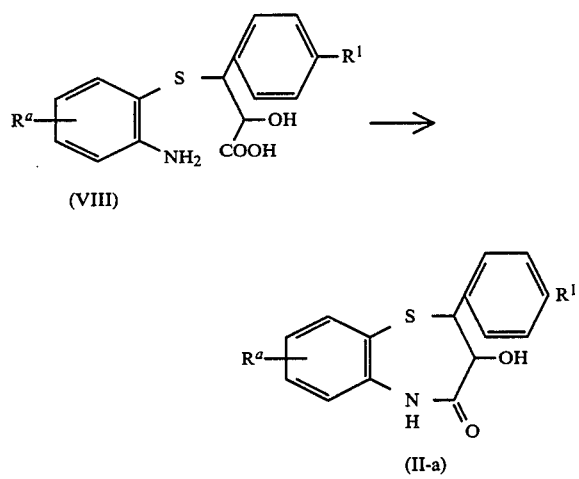

| Nos. | $R^1$ | $R^a$ | Optical isomer | M.p., etc. |
|---|---|---|---|---|
| i | OCH$_3$ | 8-CH$_3$ | − | 224–226° C. (decomp., recrystallized from ethyl acetate) $[\alpha]_D^{20}$ −123.7° (c=0.414, dimethylformamide) |
| ii | OCH$_3$ | 7-CH$_3$ | + | 213–216° C. (decomp., recrystallized from ethyl acetate) $[\alpha]_D^{20}$ +123.0° (c=0,246, dimethylformamide) |
| iii | OCH$_3$ | 7-CH$_3$ | − | 212–215° C. (decomp., recrystallized from ethyl acetate) $[\alpha]_D^{20}$ −123.7° (c=0.358, dimethylformamide) |
| iv | CH$_3$ | 8-CH$_3$ | ± | 182–184° C. (recrystallized from dimethylformamide-ethanol) |

Note:
The compounds listed in the Table are all cis isomers.

PREPARATION 12

A mixture of 1.5 g of sodium hydride (63% oil dispersion) and 25 ml of dimethylsulfoxide is heated at 70° C. for 50 minutes in argon atmosphere. A solution of 7 g of methyl (±)-threo-2-hydroxy-3-(2-amino-5-methylthiophenylthio)-3-(4-methoxyphenyl)propionate in 12 ml of dimethylsulfoxide is added dropwise to the mixture under cooling. The mixture is stirred at room temperature for 20 minutes. After the reaction is completed, the mixture is poured into ice-water. The precipitated crystals are collected by filtration, washed with water, dried and then recrystallized from a mixture of dimethylformamide and ethanol. 6.7 g of (±)-cis-2-(4-methoxyphenyl)-3-hydroxy-8-methylthio-2,3-dihydro-1,5-benzothiazepin-4(5H)-one are obtained.

M.p. 183°-184° C.

The following compound is obtained from the corresponding starting material in the same manner as above.

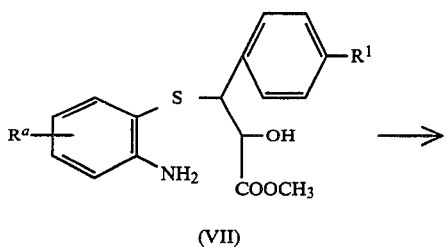

(VII)

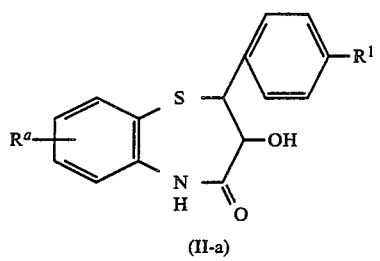

(II-a)

| | | Compound (II-a) | | |
|---|---|---|---|---|
| Nos. | $R^1$ | $R^a$ | Optical isomer | M.p., etc. |
| i | OCH$_3$ | 7-SCH$_3$ | ± | 211–214° C. (recrystallized from dimethylformamide-ethanol) |

Note:
The compound listed in the Table is cis isomer.

PREPARATION 13

A mixture of 0.54 g of (±)-threo-2-hydroxy-3-(2-amino-5-methoxyphenylthio)-3-(4-methoxyphenyl)propionic aid, 0.048 g of N-hydroxybenzotriazole monohydrate and 10 ml of dimethylformamide is cooled to 0° to 3° C., and 0.442 g of N,N'-dicyclohyxylcarbodiimide is added thereto. The mixture is stirred at the same temperature for 8 hours, and then further stirred at room temperature for 24 hours. After the reaction is completed, the precipitated crystals are collected by filtration and washed with ethyl acetate. The filtrate and the washing are combined and washed with an aqueous 5% sodium bicarbonate solution and water, successively. The solution is dried and then evaporated to remove solvent. The crystals and residue obtained above are combined and recrystallized from acetone. 0.382 g of (±)-cis-2-(4-methoxyphenyl)-3-hydroxy-8-methoxy-2,3-dihydro-1,5-benzothiazepin-4(5H)-one is obtained.
M.p. 204°–206° C.

PREPARATION 14

(a) A mixture of 4 g of (±)-cis-2-(4-methoxyphenyl)-3-hydroxy-8-methoxy-2,3-dihydro-1,5-benzothiazepin-4(5H)-one, 13 ml of pyridine and 5 ml of methylene chloride is cooled with ice-water, and 4 g of (S)-1-(2-naphthylsulfonyl)pyrrolidine-2-carbonyl chloride (prepared from (S)-1-(2-naphthylsulfonylpyrrolidine-2-carboxylic acid and oxalyl chloride in anhydrous benzene) are added thereto. The mixture is stirred at room temperature for 3 hours. After the reaction is completed, water and a mixture of ethyl acetate and chloroform (1:1) are added to the mixture. The organic layer is collected therefrom and washed with 10% hydrochloric acid, water, an aqueous 5% sodium bicarbonate solution and water, successively. The solution is dried and then evaporated. The residue is dissolved in benzene, and the precipitated crystals (3.7 g, M.p. 148°–150° C. (recrystallized from ethyl acetate), [α]$_D^{20}$−28.5° (c=0.755, chloroform)) are collected by filtration (The mother liquor is referred as "Mother liquor I". ).

A mixture of 3.6 g of the crystals obtained above, 5 ml of chloroform, 50 ml of ethanol and 50 ml of an aqueous 5% sodium hydroxide is stirred at room temperature for 1 hour. After the reaction is completed, the mixture is washed with water, dried and then evaporated. The residue is recrystallized from ethyl acetate. 1.46 g of (−)-cis-2-(4-methoxyphenyl)-3-hydroxy-8-methoxy-2,3-dihydro-1,5-benzothiazepin-4(5H)-one are obtained.
M.p. 187°–189° C.
[α]$_D^{20}$−98.7° (c=0.290, dimethylformamide)

(b) Mother liquor I (benzene solution) is evaporated and the residue is chromatographed on silica gel, whereby 3.4 g of the product (oil, [α]$_D^{20}$−68.5° (c=0.539, chloroform)) are obtained.

3.3 g of the product obtained above, 5 ml of chloroform, 50 ml of ethanol and 50 ml of an aqueous 5% sodium hydroxide are treated in the same manner as described in Paragraph (a). 1.3 g of (+)-cis-2-(4-methoxyphenyl)-3-hydroxy-8-methoxy-2,3-dihydro-1,5-benzothiazepin-4(5H)-one are obtained.
M.p. 187°–190° C. (recrystallized from ethyl acetate)
[α]$_D^{20}$+99.0° (c=0.257, dimethylformamide)

PREPARATION 15 TO 21

The following compounds are obtained from the corresponding starting materials in the same manner as described in Preparation 1.

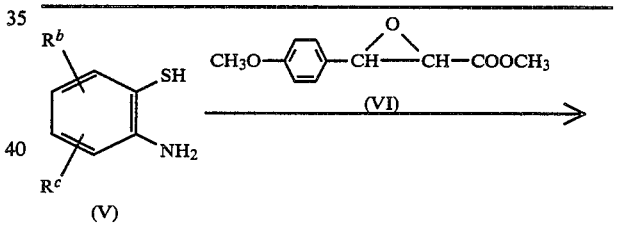

(V)

(VI)

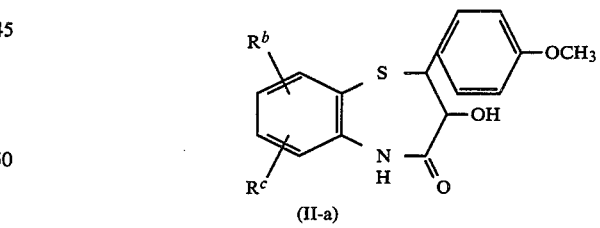

(II-a)

| Preparation Nos. | $R^b$, $R^c$ | Compound (II-a) M.p., etc. |
|---|---|---|
| 15 | 7,8-(CH$_3$)$_2$ | Cis-isomer: 221–224° C. (decomp., recrystallized from a mixture of chloroform and dimethylformamide) Trans-isomer: 235–237° C. (decomp, recrystallized from a mixture of ethyl acetate and n-hexane) |
| 16 | 7,8-(CH$_3$O)$_2$ | Cis-isomer: 240–241.5° C. (decomp., recrystallized from a mixture of dimethylformamide and ethanol) |
| 17* | 6,7-(CH$_3$)$_2$ | Cis-isomer: 235–238° C. (recrystallized from ethyl acetate) Trans-isomer: 270–271° C. |
| 18** | 6,8-(CH$_3$)$_2$ | Cis-isomer: 208–210° C. (recrystallized from ethyl acetate) Trans-isomer: 161–163° C. |
| 19*** | 7,9-(CH$_3$)$_2$ | Cis-isomer: 246–249° C. |

$R^b$—C₆H₃(SH)(NH₂)—$R^c$ (V)  +  CH₃O—C₆H₄—CH(—O—)CH—COOCH₃ (VI) →

(II-a): $R^b$, $R^c$ substituted benzene—S—CH(C₆H₄-OCH₃)—CH(OH)—C(=O)—NH— (fused ring)

| Preparation Nos. | $R^b$, $R^c$ | Compound (II-a) M.p., etc. |
|---|---|---|
| 20 | 7,8-Cl₂ | Trans-isomer: 227–230° C. Cis-isomer: 239–243° C. (decomp., recrystallized from a mixture of chloroform and ethanol) (turbid melt at 210° C.) |
| 21 | 8,9-Cl₂ | Cis-isomer: 207–209° C. (recrystallized from a mixture of chloroform and ethanol) Trans-isomer: 244–249° C. |

Note:
The compounds listed in the Table are all racemic compounds.
*Methyl (±)-threo-2-hydroxy-3-(2-amino-3,4-dimethyl-phenylthio)-3-(4-methoxyphenyl)propionate is obtained in addition to the compounds listed above. M.p. 109–111.5° C. (recrystallized from isopropanol)
**Methyl (±)-threo-2-hydroxy-3-(2-amino-3,5-dimethyl-phenylthio)-3-(4-methoxyphenyl)propionate is obtained in addition to the compounds listed above. M.p. 109–113° C. (recrystallized from isopropyl ether)
***Methyl (±)-threo-2-hydroxy-3-(2-amino-4,6-dimethyl-phenylthio)-3-(4-methoxyphenyl)propionate is obtained in addition to the compound listed above. M.p. 130–133° C.

PREPARATION 22

(a) A mixture of 49.52 g of 2-amino-4,5-dimethylthiophenol, 47.49 g of methyl (±)-trans-3-(4-methoxyphenyl)glycidate and 500 ml of toluene is heated at 95°–100° C. for 23 hours. After cooling, the precipitated crystals (Cyrstals I) are collected by filtration, and the filtrate is evaporated to remove solvent. The residue is digested with diisopropyl ether, and the crystals thus obtained (Crystals II) are collected by filtration. Crystals I and Crystals II are combined and then recrystallized from a mixture of ethyl acetate and n-hexane. 58.95 g of methyl (±)-threo-2-hydroxy-3-(2-amino-4,5-dimethylphenylthio)-3-(4-methoxyphenyl)propionate are obtained.

M.p. 111°–114° C.

(b) A mixture of 58.9 g of methyl (±)-threo-2-hydroxy-3-(2-amino-4,5-dimethylphenylthio)-3-(4-methoxyphenyl)propionate, 590 ml of an aqueous 5% sodium hydroxide solution and 590 ml of ethanol is stirred at room temperature for 2 hours. After the reaction is completed, the mixture is adjusted to pH 3 with 10% hydrochloric acid. The precipitated crystals are collected by filtration, washed with water and then dried. 54.2 g of (±)-threo-2-hydroxy-3-(2-amino-4,5-dimethylphenylthio)-3-(4-methoxyphenyl)propionic acid are obtained.

M.p. 163°–168° C.

(c) 31.3 g of L-(p-hydroxyphenyl)glycine methyl ester hydrochloride are dissolved in 750 ml of methanol. A solution of 8.08 g of potassium hydroxide in 375 ml of methanol is added to the solution, and the precipitates (inorganic materials) are removed by filtration. 25 g of (±)-threo-2-hydroxy-3-(2-amino-4,5-dimethylphenylthio)-3-(4-methoxyphenyl)propionic acid are added to the filtrate, and 375 ml of methanol are added thereto to make a clear solution. The clear solution is evaporated under reduced pressure to remove solvent. The residue is recrystallized three times from ethanol (the mother liquor is referred to as "Mother liquor I"), whereby 10.2 g of (+)-threo-2-hydroxy-3-(2-amino-4,5-dimethylphenylthio)-3-(4-methoxyphenyl)propionic acid.L-(p-hydroxyphenyl)glycine methyl ester salt are obtained.

M.p. 173°–175° C. (decomp.)

$[\alpha]_D^{20} + 290.8°$ (C=0.410, dimethylformamide)

The product obtained above is dissolved in 10% hydrochloric acid, and the solution is adjusted to pH 4 with potassium carbonate. The precipitated crystals are collected by filtration, washed with water and then dried. 4.7 g of (+)-threo-2-hydroxy-3-(2-amino-4,5-dimethylphenylthio)-3-(4-methoxyphenyl)propionic acid are obtained.

M.p. 167°–169° C. (decomp.)

$[\alpha]_D^{20} + 361.2°$ (C=0.556, N-NaOH)

Mother liquor I (ethanol solution) is evaporated under reduced pressure to remove solvent. The residue is dissolved in 10% hydrochloric acid, and the solution is adjusted to pH 4 with potassium carbonate. The precipitated crystals are collected by filtration. Then, a mixture of the crystals (13.3 g) thus obtained, 16.7 g of D-(p-hydroxyphenyl)glycine methyl ester hydrochloride and 4.3 g of potassium hydroxide is treated in the same manner as above. The crude product thus obtained is recrystallized from ethanol, whereby 8.97 g of (−)-threo-2-hydroxy-3-(2-amino-4,5-dimethylphenylthio)-3-(4-methoxyphenyl)propionic acid. D-(p-hydroxyphenyl)glycine methyl ester salt are obtained.

M.p. 170°–174° C. (decomp.)

$[\alpha]_D^{20} - 222.1°$ (C=0.664, dimethylformamide)

The product obtained above are converted to its free acid in the same manner as above, whereby 2.66 g of (−)-threo-2-hydroxy-3-(2-amino-4,5-dimethylphenylthio)-3-(4-methoxyphenyl)propionic acid are obtained.

M.p. 154°–157° C. (decomp.)

$[\alpha]_D^{20} - 316.8°$ (C=0.512, N-NaOH)

(d-1) A mixture of 4.7 g of (+)-threo-2-hydroxy-3-(2-amino-4,5-dimethylphenylthio)-3-(4-methoxyphenyl)propionic acid and 80 ml of xylene is refluxed for 24 hours. The resulting water is removed during the reaction. After the reaction is completed, the mixture is evaporated to remove solvent. 3.95 g of (+)-cis-2-(4-methoxyphenyl)-3-hydroxy-7,8-dimethyl-2,3-dihydro-1,5-benzothiazepin-4(5H)-one are obtained.

M.p. 232°–234° C. (decomp.)

$[\alpha]_D^{20} + 131.4°$ (C=0.778, dimethylformamide)

(d-2) A mixture of 2.6 g of (−)-threo-2-hydroxy-3-(2-amino-4,5-dimethylphenylthio)-3-(4-methoxyphenyl)propionic acid and 45 ml of xylenen is treated in the same manner as described in paragraph (d-1). 1.98 g of (−)-cis-2-(4-methoxyphenyl)-3-hydroxy-7,8-dimethyl-2,3-dihydro-1,5-benzothiazepin-4(5H)-one are obtained.

M.p. 225°–227° C. (decomp.)

$[\alpha]_D^{20} - 127.2°$ (C=0.66, dimethylformamide)

PREPARATION 23 TO 24

The following compounds are obtained from the corresponding starting materials in the same manner as described in Preparation 1.

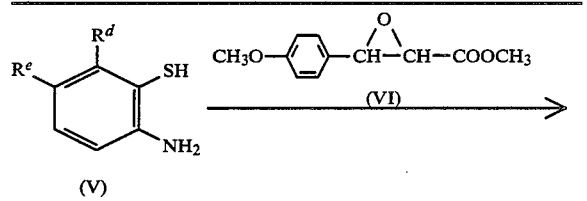

| Prepara-tion Nos. | Compound (II-a) | | |
|---|---|---|---|
| | $R^d$ | $R^e$ | M.p., etc. |
| 23 | H | F | Cis-isomer: 215–218° C. (recrystallized from a mixture of dimethylformamide and ethanol) |
| 24* | F | H | Cis-isomer: 218–222° C. (recrystallized from a mixture of dimethylformamide and ethanol) (turbid melt at 208° C.) Trans-isomer: 231–235° C. (recrystallized from a mixture of dimethylformamide and ethanol) (turbid melt at 215° C.) |

Note:
The compounds listed in the Table are all racemic compounds.
*Methyl (±)-threo-2-hydroxy-3-(2-amino-6-fluorophenylthio)-3-(4-methoxyphenyl)propionate is obtained in addition to the compounds listed above. M.p. 110–112° C. (recrystallized from ethanol)

PREPARATION 25

A mixture of 0.683 g of sodium hydride (63% oil dispersion) and 12 ml of dimethylsulfoxide is stirred at 70° C. for 45 minutes. After cooling, a solution of 3 g of methyl (±)-threo-2-hydroxy-3-(2-amino-6-fluorophenylthio)-3-(4-methoxyphenyl)propionate in 7 ml of dimethylsulfoxide is added dropwise to the mixture, and said mixture is stirred at room temperature for 5 minutes. After the reaction is completed, the mixture is poured into ice-water. The aqueous mixture is adjusted to a pH of about 7 with acetic acid, and the precipitated crystals are collected by filtration. Said crystals are washed with water and n-hexane and then dried. 2.39 g of (±)-cis-2-(4-methoxyphenyl)-3-hydroxy-9-fluoro-2,3-dihydro-1,5-benzothiazepin-4(5H)-one are obtained.

The physico-chemical properties of this product are identical with those of the product obtained in Preparation 24.

PREPARATION 26

A solution of 500 mg of (±)-cis-2-(4-methoxyphenyl)-3-hydroxy-8-methoxy-2,3-dihydro-1,5-benzothiazepin-4(5H)-one and 358 mg of pyridine in 8 ml of dimethylformamide is ice-cooled, and a solution of 130 mg of acetyl chloride in 2 ml of dimethylformamide is dropwise added thereto. The mixture is stirred at room temperature for one hour. After the reaction is completed, the mixture is poured into ice-water. The aqueous mixture is extracted with chloroform, and the extract is washed with 10% hydrochloric acid and water, successively. Then, the extract is dried and evaporated under reduced pressure to remove solvent. The residue is recrystallized from a mixture of dimethylformamide and ethanol. 465 mg of (±)-cis-2-(4-methoxyphenyl)-3-acetoxy-8-methoxy-2,3-dihydro-1,5-benzothiazepin-4(5H)-one ⅓ hydrate are obtained.

M.p. 218°–219° C.

PREPARATION 27

226 mg of (±)-cis-2-(4-methoxyphenyl)-3-hydroxy-7,8-dimethyl-2,3-dihydro-1,5-benzothiazepin-4(5H)-one are suspended in 2 ml of pyridine, and 59 mg of acetyl chloride are added thereto under ice-cooling. The mixture is stirred at room temperature for 2 hours. After the reaction is completed, ethyl acetate-chloroform (1:1) is added to the reaction mixture. The mixture is washed with 10% hydrochlric acid and water, successively. Then, the mixture is dried and evaporated under reduced pressure to remove solvent. 219 mg of (±)-cis-2-(4-methoxyphenyl)-3-acetoxy-7,8-dimethyl-2,3-dihydro-1,5-benzothiazepin-4(5H)-one are obtained.

M.p. 227°–229° C.

What we claim is:

1. A 1,5-benzothiazepine of the formula:

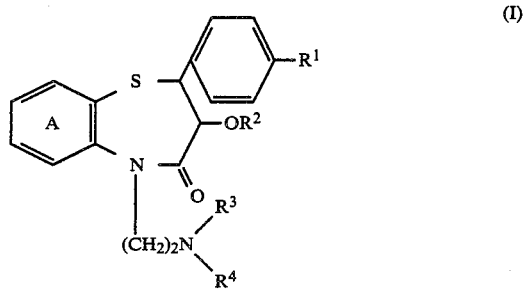

wherein $R^1$ is lower alkyl or lower alkoxy, $R^2$ is lower alkanoyl, each one of $R^3$ and $R^4$ is lower alkyl, Ring A is a substituted benzene ring of the formula:

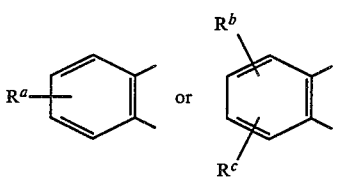

$R^a$ is lower alkyl or lower alkoxy, and each one of $R^b$ and $R^c$ is lower alkyl or a pharmaceutically acceptable acid addition salt thereof.

2. A compound according to claim 1, in which $R^1$ is methyl or methoxy.

3. A compound according to claim 2, in which $R^a$ is methyl or methoxy, and $R^b$ and $R^c$ are methyl.

4. A compound according to claim 2, in which Ring A is a substituted benzene ring of the formula:

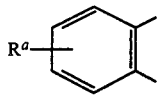

, wherein $R^a$ is methyl or methoxy.

5. A compound according to claim 3, in which $R^2$ is acetyl, and $R^3$ and $R^4$ are methyl.

6. A cis isomer of a compound claimed in any one of claims 1 through 5.

7. A (+)-cis isomer of a compound claimed in any one of claims 1 through 5.

8. A compound according to claim 5, which is selected from (±)-cis-2-(4-methylphenyl)-3-acetoxy-5-[2-(dimethylamino)ethyl]-8-methoxy-2,3-dihydro-1,5-benzothiazepin-4(5H)-one, (±)-cis-2-(4-methoxyphenyl)-3-acetoxy-5-[2-(dimethylamino)ethyl]-8-methyl-2,3-dihydro-1,5-benzothiazepin-4(5H)-one, (±)-cis-2-(4-methoxyphenyl)-3-acetoxy-5-[2-(dimethylamino)ethyl]-7-methyl-2,3-dihydro-1,5-benzothiazepin-4(5H)-one, (±)-cis-2-(4-methoxyphenyl)-3-acetoxy-5-[2-(dimethylamino)ethyl]-7-methoxy-2,3-dihydro-1,5-benzothiazepin-4(5H)-one, (±)-cis-2-(4-methoxyphenyl)-3-acetoxy-5-[2-(dimethylamino)ethyl]-8-methoxy-2,3-dihydro-1,5-benzothiazepin-4(5H)-one, (±)-cis-2-(4-methoxyphenyl)-3-acetoxy-5-[2-(dimethylamino)ethyl]-6-methoxy-2,3-dihydro-1,5-benzothiazepin-4(5H)-one, (+)-cis-2-(4-methoxyphenyl)-3-acetoxy-5-[2-(dimethylamino)ethyl]-8-methyl-2,3-dihydro-1,5-benzothiazepin-4(5H)-one, (+)-cis-2-(4-methoxyphenyl)-3-acetoxy-5-[2-(dimethylamino)ethyl]-7-methyl-2,3-dihydro-1,5-benzothiazepin-4(5H)-one, (+)-cis-2-(4-methoxyphenyl)-3-acetoxy-5-[2-(dimethylamino)ethyl]-8-methoxy-2,3-dihydro-1,5-benzothiazepin-4(5H)-one, (±)-cis-2-(4-methoxyphenyl)-3-acetoxy-5-[2-(dimethylamino)ethyl]-7,8-dimethyl-2,3-dihydro-1,5-benzothiazepin-4(5H)-one, (+)-cis-2-(4-methoxyphenyl)-3-acetoxy-5-[2-(dimethylamino)ethyl]-7,8-dimethyl-2,3-dihydro-1,5-benzothiazepin-4(5H)-one, (±)-cis-2-(4-methoxyphenyl)-3-acetoxy-5-[2-(dimethylamino)ethyl]-6,7-dimethyl-2,3-dihydro-1,5-benzothiazepin-4(5H)-one, or a pharmaceutically acceptable acid addition salt thereof.

9. A 1,5-benzothiazepine of the formula:

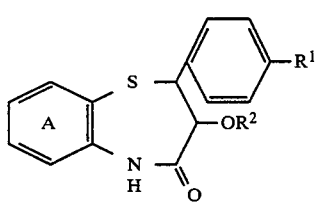

wherein $R^1$ is lower alkyl or lower alkoxy, $R^2$ is hydrogen atom or lower alkanoyl and Ring A is a substituted benzene ring of the formula:

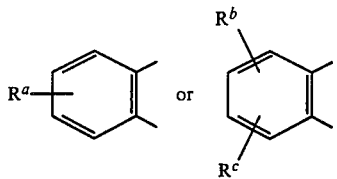

$R^a$ is lower alkyl or lower alkoxy and each one of $R^b$ and $R^c$ is lower alkyl, or a salt thereof.

10. A 1,5-benzothiazepine of the formula:

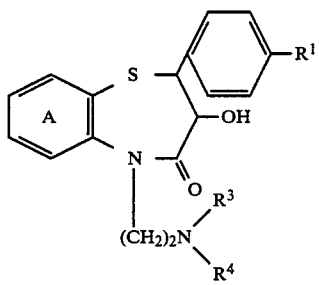

wherein $R^1$ is lower alkyl or lower alkoxy, each one of $R^3$ and $R^4$ is lower alkyl, Ring A is a substituted benzene ring of the formula:

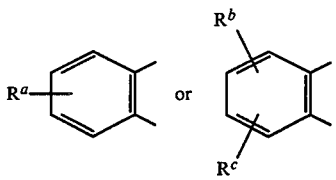

wherein $R^a$ is lower alkyl or lower alkoxy and each one of $R^b$ and $R^c$ is lower alkyl, or a salt thereof.

11. A compound according to claim 1 which is: ±cis-2-(4 methoxyphenyl)-3-acetoxy-5-[-2-(dimethylamino)ethyl]-6-methyl-2,3-dihydro-1,5-benzothiazepin-4(5H)-one or its pharmaceutically acceptable salt.

12. A pharmaceutical composition possessing hypotensive, cerebral vasodilating or coronary vasodilating activity which comprises a therapeutically effective amount of a compound according to claim 1 and a pharmaceutically acceptable carrier therefor.

13. A method of producing a hypotensive effect on a warm-blooded animal comprising administering to said warm-blooded animal an effective amount of a compound claimed in claim 1.

14. A method of producing a cerebral vasodilating effect on a warm-blooded animal comprising administering to said warm-blooded animal an effective amount of a compound claimed in claim 1.

15. A method of producing a coronary vasodilating effect on a warm-blooded animal comprising administering to said warm-blooded animal an effective amount of a compound claimed in claim 1.

* * * * *